(12) United States Patent
Sun et al.

(10) Patent No.: US 7,329,646 B2
(45) Date of Patent: Feb. 12, 2008

(54) DERIVATIVES OF THE INSULINOTROPIC PEPTIDE EXENDIN-4 AND METHODS OF PRODUCTION THEREOF

(75) Inventors: Yukun Sun, Shanghai (CN); Dengxi Wu, Shanghai (CN); Wen Chen, Shanghai (CN); Zhiyong Zhu, Shanghai (CN)

(73) Assignee: Shanghai Huayi Bio-Lab Co., Ltd., Shanghai (CN)

( * ) Notice: Subject to any disclaimer, the term of this patent is extended or adjusted under 35 U.S.C. 154(b) by 174 days.

(21) Appl. No.: 10/704,409

(22) Filed: Nov. 7, 2003

(65) Prior Publication Data

US 2004/0142866 A1 Jul. 22, 2004

Related U.S. Application Data

(63) Continuation-in-part of application No. PCT/CN02/00316, filed on May 8, 2002.

(30) Foreign Application Priority Data

May 10, 2001 (CN) .................... 01 1 12856

(51) Int. Cl.
*A61K 38/22* (2006.01)
*C07K 14/575* (2006.01)
(52) U.S. Cl. .................... 514/12; 514/21; 530/324
(58) Field of Classification Search ................ None
See application file for complete search history.

(56) References Cited

U.S. PATENT DOCUMENTS

| 5,424,286 | A | 6/1995 | Eng | ............... 514/2 |
|---|---|---|---|---|
| 6,265,204 | B1 * | 7/2001 | Ward et al. | ............. 435/254.11 |
| 6,329,336 | B1 | 12/2001 | Bridon et al. | .................. 514/2 |
| 6,506,724 | B1 | 1/2003 | Hiles et al. | ...................... 514/2 |
| 6,514,500 | B1 | 2/2003 | Bridon et al. | ............. 424/193.1 |
| 6,528,486 | B1 | 3/2003 | Larsen et al. | ................. 514/12 |
| 6,593,295 | B2 | 7/2003 | Bridon et al. | .................. 514/2 |

FOREIGN PATENT DOCUMENTS

| WO | WO 95/17510 A1 * | 6/1995 |
|---|---|---|
| WO | WO 99/25727 A2 * | 5/1999 |
| WO | 01/04156 | 1/2001 |
| WO | WO 02/90388 A1 * | 11/2002 |
| WO | 03/016349 | 2/2003 |

OTHER PUBLICATIONS

"Isolation and Characterization of Exendin-4, an Exendin-3 Analogue, from *Heloderma suspetum* Venom" by J. Eng, et al., *The Journal of Biological Chemistry*, vol. 267, No. 11, pp. 7402-7406 (1992).

(Continued)

*Primary Examiner*—Jeffrey Edwin Russel
(74) *Attorney, Agent, or Firm*—Zhaohui Wang; Perkins Coie LLP

(57) ABSTRACT

The present invention is directed to the development of novel exendin-4 derivatives exhibiting advantageous glucose-regulatory properties, and to methods of producing these derivatives, including recombinant methods in which these derivatives are produced by cleavage of a fusion protein containing multiple copies of the exendin-4 derivative peptide. The methods of the present invention can be used to simplify the process of producing the disclosed exendin-4 derivatives, thereby lowering the cost of their production.

7 Claims, 8 Drawing Sheets

```
                      5          10         15         20         25         30         35        40
GLP-1 (7-36):      H A E G T  F T S D V  S Y L E  G Q A A K  E F I A W  L V K G R

Exendin-4 (WT):    H G E G T  F T S D L  S K Q M E  E E A V R  L F I E W  L K N G G  P S S G A  P P P S SEQ ID NO. 6:      H G E G T  F T S D L  S K Q M E  E E A V K  L F I E W  L K N G G  P S S G A  P P P S R SEQ ID NO. 7:      H G E G T  F T S D L  S K Q M E  E E A V H  L F I E W  L K N G G  P S S G A  P P P S R SEQ ID NO. 8:      H G E G T  F T S D L  S K Q L E  E E A V K  L F I E W  L K N G G  P S S G A  P P P S R
```

OTHER PUBLICATIONS

"Glucose-Lowering and Insulin-Sensitizing Actions of Exendin-4" by A. Young, et al., *Diabetes*, vol. 48, pp. 1026-1034 (May 1999).

"The Glucagon-Like Peptides" by Timothy James Kieffer and Joel Francis Habener, *Endocrine Reviews*, vol. 20, No. 6, pp. 876-913 (Dec. 1999).

\* cited by examiner

| | | 5 | | 10 | | 15 | | 20 | | 25 | | 30 | | 35 | | 40 |
|---|---|---|---|---|---|---|---|---|---|---|---|---|---|---|---|---|
| GLP-1 (7-36): | H A E G T | F T S D V | S S Y L E | G Q A A K | E F I A W | L V K G R | | | |
| Exendin-4 (WT): | H G E G T | F T S D L | S K Q M E | E E A V R | L F I E W | L K N G G | P S S G A | P P P S |
| SEQ ID NO. 6: | H G E G T | F T S D L | S K Q M E | E E A V K | L F I E W | L K N G G | P S S G A | P P P S R |
| SEQ ID NO. 7: | H G E G T | F T S D L | S K Q M E | E E A V H | L F I E W | L K N G G | P S S G A | P P P S R |
| SEQ ID NO. 8: | H G E G T | F T S D L | S K Q L E | E E A V K | L F I E W | L K N G G | P S S G A | P P P S R |

*FIG. 1*

```
            MetHisGlyGluGlyThrPheThrSerAspLeuSerLysGlnLeu
AATTCC ATGCACGGCGAAGGCACCTTCACCAGCGATCTGAGCAAACAGCTG
EcoRI

GluGluGluAlaValLysLeuPheIleGluTrpLeuLysAsnGlyGlyProSerSerGly
GAAGAAGAAGCGGTTAAACTGTTCATCGAATGGCTGAAAAACGGCGGCCCGAGCAGCGGC

AlaProProProSerArg...
GCGCCGCCGCCGAGCCGTTAGA
                   HindIII
```

```
            MetArgHisGlyGluGlyThrPheThrSerAspLeuSerLysGlnMet.
AATTCCAGATCTATGCGTCACGGCGAAGGCACCTTCACCAGCGATCTGAGCAAACAGATG
EcoRI BglII

GluGluGluAlaValLysLeuPheIleGluTrpLeuLysAsnGlyGlyProSerSerGly
GAAGAAGAAGCGGTTAAACTGTTCATCGAATGGCTGAAAAACGGCGGCCCGAGCAGCGGC

AlaProProProSerArgGlySer...
GCGCCGCCGCCGAGCCGTGGATCCTAG
                BamHI
```

Fig. 5

DERIVATIVES OF THE INSULINOTROPIC PEPTIDE EXENDIN-4 AND METHODS OF PRODUCTION THEREOF

CROSS-REFERENCE TO RELATED APPLICATIONS

This application is a continuation-in-part of PCT/CN02/00316, which bears an international filing date of 8 May 2002, and which claims priority to Chinese Patent Application Serial No. 01112856.9, filed May 10, 2001.

BACKGROUND OF THE INVENTION

Glucagon-like peptide-1 ("GLP-1") is a peptide hormone secreted by intestinal cells that has been shown in multiple studies to produce an enhancing effect on insulin secretion. Such studies have also shown that GLP-1 has more advantages than insulin in the treatment of type II diabetes mellitus. Most notably, GLP-1 is observed to be capable of enhancing β-cell division and therefore increasing β-cell counts, effects which have not been found in other medicines used for the treatment of diabetes. In addition, GLP-1 is effective in those patients who do not respond to treatment by the administration of sulfonylurea. Furthermore, because administration of GLP-1 does not enhance insulin secretion when the concentration of blood glucose is restored to normal levels, treatment with GLP-1 does not result in hypoglycemia. Therefore, in light of these and other data, GLP-1 is regarded as a desirable medicine to treat diabetes mellitus.

Exendin-4 is a 39 amino acid C-terminal amidated peptide analog of GLP-1 found in the venom of the Gila Monster (*Heloderma horridum*), with a 53% amino acid sequence homology to the GLP-1 peptide sequence. See, e.g., Eng, J., et al. "Isolation and Characterization of Exendin-4, and Exendin-3 Analogue from *Heloderma suspectum* Venom," *J. Bio. Chem.*, 267:11, p. 7402-7405 (1992), Young, A. A., et al., "Glucose-Lowering and Insulin-Sensitizing Actions of Exendin-4," *Diabetes*, Vol. 48, p. 1026-1034, May, 1999. In terms of its activity, exendin-4 is a highly specific agonist for the GLP-1 receptor, and, like GLP-1, is able to stimulate insulin secretion. Therefore, like GLP-1, exendin-4 is regarded as an insulinotropic peptide.

However, unlike GLP-1, exendin-4 has a relatively long half-life in humans, because of its resistance to the dipeptidyl peptidase IV which rapidly degrades the GLP-1 sequence in vivo. Furthermore, it has been shown that, as compared to GLP-1, exendin-4 has a stronger capability to stimulate insulin secretion, and that a lower concentration of exendin-4 may be used to obtain such stimulating activity. See, e.g., U.S. Pat. No. 5,424,286, herein incorporated by reference. Therefore exendin-4 peptides or derivatives thereof (for examples of such derivatives see, e.g., U.S. Pat. No. 6,528,486, herein incorporated by reference, and its corresponding international application WO 01/04156) have a greater potential utility for the treatment of conditions involving the dysregulation of insulin levels (e.g., conditions such as diabetes) than either insulin or GLP-1.

In the present invention, several novel exendin-4 derivative sequences are disclosed which have been found to exhibit significant blood-glucose regulatory effects, including the ability to regulate blood glucose levels for long durations (i.e., long half-life) without hypoglycemic effects. In addition, the present invention discloses a novel recombinant method of producing such exendin-4 derivative sequences by producing these sequences as fusion proteins, which are then cleaved with the appropriate reagent to yield separate copies of the desired peptide sequence. In one aspect of this method, a novel procedure for producing exendin-4 fusion proteins that are cleaved by trypsin is disclosed.

BRIEF SUMMARY OF THE INVENTION

The present invention is directed to exendin-4 and exendin-4 derivatives exhibiting glucose-regulatory properties, and to recombinant methods of producing these exendin-4 sequences and exendin-4 derivatives.

One embodiment of the invention is directed to exendin-4 derivative peptides that are altered to remove all internal cleavage sites for a cleavage reagent while preserving the exendin-4-like activity of the exendin-4 derivative peptide. In this embodiment, the cleavage reagent includes cyanogen bromide, alkaline protease such as trypsin, enterokinase, and clostripain. When the cleavage reagent is trypsin, the alteration to remove all the internal cleavage sites is accomplished by replacement of the Arg and Lys residue or residues of the exendin-4 derivative sequence with non-Arg and non-Lys amino acids or amino acid derivatives. Alternatively, when the cleavage reagent is trypsin the Arg residue or residues of the exendin-4 derivative sequence may be replaced with non-Arg amino acids or amino acid derivatives and any Lys residues in the exendin-4 derivative sequence may be protected by acetylation. Examples of peptide sequences contemplated include the peptides of SEQ ID NOS:3-8.

In another embodiment, the present invention is directed to fusion peptides comprising at least two tandemly linked peptides that are altered to remove all internal cleavage sites for a cleavage reagent while preserving the exendin-4-like activity of the exendin-4 derivative peptide, as well as isolated DNA sequences comprising a DNA sequence encoding these peptides, expression vectors comprising these isolated DNA sequences, and transformed host cells comprising these expression vectors.

In still another embodiment, the present invention includes a method for producing the exendin-4 derivative peptide of claim 1, either by expressing a single copy of the exendin-4 derivative in an expression vector or, alternatively, by expressing a fusion protein containing multiple copies of the exendin-4 derivative and then cleaving this fusion protein into individual copies of the exendin-4 sequence using the appropriate cleavage reagent. Cleavage reagents include, but are not limited to, cyanogen bromide, alkaline proteases such as trypsin, enterokinase, and clostripain.

BRIEF DESCRIPTION OF THE DRAWINGS

FIG. 1 illustrates aligned amino acid sequences of GLP-1 (7-36) (SEQ ID NO:9), wild-type exendin-4 (SEQ ID NO:1), and three inventive derivatives of wild-type exendin-4, namely, exendin-4 (Lys$_{20}$, Arg$_{40}$) (SEQ ID NO:6), exendin-4 (His$_{20}$, Arg$_{40}$) (SEQ ID NO:7), and exendin-4 (Leu$_{14}$, Lys$_{20}$, Arg$_{40}$) (SEQ ID NO:8). In this figure, shaded amino acids in the GLP-1 (7-36) and wild-type exendin-4 sequences indicates amino acids present in both sequences, while underlined amino acids in the three inventive derivatives of wild-type exendin-4 indicate substituted or added amino acids in these peptide sequences.

FIG. 5 shows the peptide and corresponding DNA sequences used to construct the exendin-4 (Leu$_{14}$, Lys$_{20}$, Arg$_{40}$) and exendin-4 (Lys$_{20}$, Arg$_{40}$) sequences. The peptide and corresponding DNA sequences used to construct the exendin-4 (Leu$_{14}$, Lys$_{20}$, Arg$_{40}$) and the exendin-4 (Lys$_{20}$, Arg$_{40}$) sequences are shown in the top and bottom panels, respectively. The DNA sequence in the top panel is given in the sequence listing as SEQ ID NO:15, while the DNA sequence in the bottom panel is given in the sequence listing as SEQ ID NO:14. Restriction sites are as indicated; changed amino acid positions relative to the wild-type exendin-4 sequence are in bold.

DETAILED DESCRIPTION OF THE INVENTION

Figure 2:
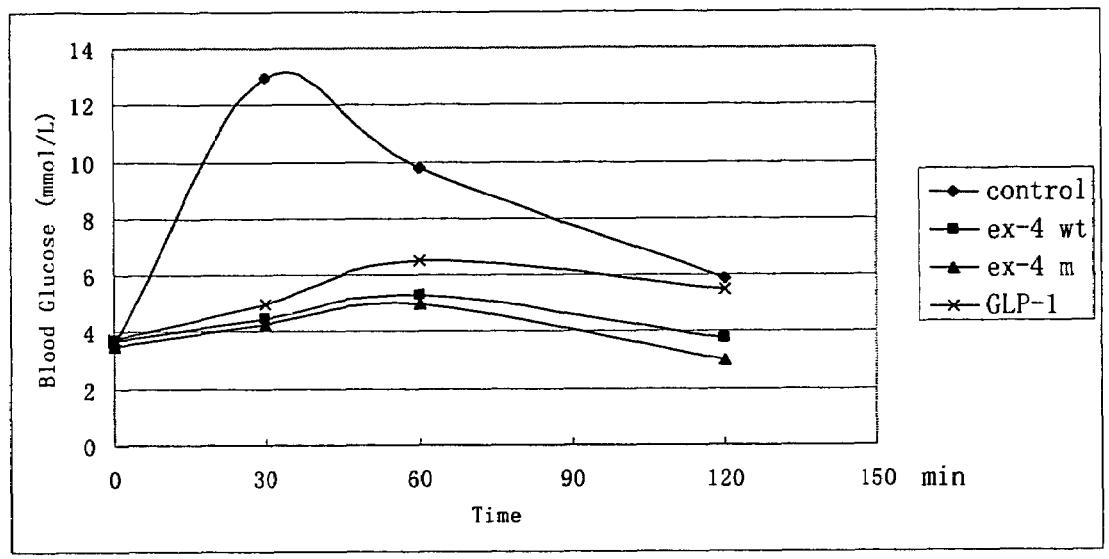
FIG. 2 shows the effects of saline control, GLP-1, wild-type exendin-4 ("ex-4 wt"), and the exendin-4 derivative exendin-4 (Leu$_{14}$, Lys$_{20}$, Arg$_{40}$) ("ex-4 m") on the blood glucose levels of non-diabetic C57 BL/6J mice after glucose challenge.

The present invention is directed to novel exendin-4 derivatives with insulinotropic properties, and to recombinant and synthetic methods for producing these exendin-4 derivatives. The recombinant methods encompass both methods directed to single copies of the genes for these peptides, and, preferably, to multiple copies of these genes that are tandemly linked so as to produce fusion proteins which are then cleaved to produce multiple copies of the desired peptide.

In the latter case, one embodiment of the present invention is specifically directed to the alteration of the sequences of these peptides to allow for the cleavage of the multimeric fusion proteins produced by these methods by trypsin, which normally is specific for either Arg or Lys residues. In the methods of the invention, Arg is added between the C-terminus of one copy of the exendin-4 peptide derivative and the N-terminus of the following copy of the exendin-4 peptide to which it is tandemly linked, and any Arg residues internal to these genes are removed or more preferably substituted by recombinant methods. In these methods it may also be necessary to remove internal Lys residues, which are also cleaved by trypsin, or to protect such residues from trypsin cleavage. One specific method of protection contemplated herein is the reversible acetylation of internal Lys residues to prevent their cleavage by trypsin.

The present invention is also directed to various pharmaceutical compositions containing the exendin-4 derivatives of the invention. Compositions containing these active compounds have therapeutic utility, particularly in the treatment of type II diabetes.

Summary of Peptide and DNA Sequences

Exendin-4 peptide sequences and derivatives thereof are presented as: the wild-type exendin-4 of SEQ ID NO:1; the exendin-4 ((Arg/Leu/Ile/Met)$_{14}$, (His/Arg/Lys)$_{20}$, (Arg-OH/—OH/—NH$_2$/Lys-OH)$_{40}$) of SEQ ID NO:2; the exendin-4 ((Ile/Leu/Met)$_{14}$, (His/Lys)$_{20}$, Arg$_{40}$) of SEQ ID NO:3; the exendin-4 ((not Lys/not Arg)$_{12}$, (not Lys/not Arg)$_{20}$, (not Lys/not Arg)$_{27}$, Arg$_{40}$) of SEQ ID NO:4; the exendin-4 ((not Lys/not Arg)$_{20}$, Arg$_{40}$) of SEQ ID NO:5; the exendin-4 (Lys$_{20}$, Arg$_{40}$) of SEQ ID NO:6; the exendin-4 (His$_{20}$, Arg$_{40}$) of SEQ ID NO:7; and, the exendin-4 (Leu$_{14}$, Lys$_{20}$, Arg$_{40}$) of SEQ ID NO:8. A detailed description of the nomenclature used to describe these exendin-4 peptide derivatives is provided elsewhere herein.

The GLP-1 (7-36) peptide sequence presented in the alignment of FIG. 1 is given in the sequence listing as SEQ ID NO:9.

The DNA sequences used in the preparation of the exendin-4 (Leu$_{14}$, Lys$_{20}$, Arg$_{40}$) of Example 2 are given in the sequence listing as SEQ ID NOS:10-13.

The DNA sequence of the bottom panel of FIG. 5 that is used in Example 9 to prepare exendin-4 (Lys$_{20}$, Arg$_{40}$) is given in the sequence listing as SEQ ID NO:14.

The DNA sequence of the top panel of FIG. 5 that is used in Example 2 to prepare exendin-4 (Leu$_{14}$, Lys$_{20}$, Arg$_{40}$) is given in the sequence listing as SEQ ID NO:15.

The six DNA sequences used in Example 9 to generate the exendin-4 (Lys$_{20}$, Arg$_{40}$) DNA sequence are given in the sequence listing as SEQ ID NOS:16-21.

Exendin-4 Derivatives

In one aspect, the present invention is directed to derivatives of the wild-type insulinotropic peptide exendin-4 (SEQ ID NO:1), and particularly to the non-limiting exendin-4 peptide derivatives of SEQ ID NOS:6-8, which are shown elsewhere herein to exhibit particularly advantageous exendin-4-like properties. As set forth in the present invention, the exendin-4 peptide derivatives contemplated herein may be prepared by synthetic chemical techniques, or by less expensive recombinant techniques that are novel to the present invention. These techniques for the preparation of the exendin-4 derivatives of the invention are set forth in detail in a separate section below.

"Exendin-4 peptide derivatives" (synonymously "exendin-4 derivatives") as used herein refers to derivatives (synonymously, "variants" or analogs") of the exendin-4 peptide (synonymously, "polypeptide" or "protein") sequence derived from and related to the wild-type exendin-4 sequence (SEQ ID NO:1). Such exendin-4 peptide derivatives may be prepared by any of the methods known to one of ordinary skill in the art, including amino acid substitutions or additions, chemical modifications, etc. Such exendin-4 derivatives are contemplated to include derivatives of the wild-type exendin-4 peptide sequence, and may also include any of the modified exendin-4 derivatives of the invention that have been subjected to further modification, e.g., any of the sequences of SEQ ID NOS:6-8 of the Examples which are further modified by additional amino acid substitutions, additions (e.g., of a poly-lysine tail as described elsewhere herein), etc. Such derivatives are further contemplated to include salts or other compositions, particularly pharmaceutical compositions as described in a separate section below.

As contemplated herein, amino acid substitutions may be obtained by substitution of one or more amino acid residue(s) of a peptide sequence. In situations where the functionality of the peptide is to be preserved, such amino acid substitutions are preferably conservative or highly conservative substitutions. As used herein, a "conservative substitution" is the replacement of an amino acid with one that has the same net electronic charge and approximately the same size and shape. A "highly conservative substitution" is the replacement of an amino acid with another amino acid that has the same functional group in the side chain and nearly the same size and shape. For example, amino acids with aliphatic or substituted aliphatic amino acid side chains have nearly the same size when the total number carbon and heteroatoms in their side chains differs by no more than two. They have nearly the same shape when they have the same number of branches in their side chains. Examples of highly conservative substitution include valine for leucine, threonine for serine, aspartic acid for glutamic acid, and phenylglycine for phenylalanine. Examples of substitutions which are not highly conservative include alanine for valine, alanine for serine, and aspartic acid for serine.

Preferably the exendin-4 variants of the present invention are functional, i.e., possess exendin-4-like activity which, as used herein, refers to the insulinotropic activity exhibited by exendin-4 or other insulinotropic peptides. In the present invention, "insulinotropic" peptides are peptides with exendin-4-like or GLP-1-like insulinotropic activity, i.e., peptides that stimulate, or cause the stimulation of, the synthesis or expression of the hormone insulin. Assays for such activity are well known to the skilled artisan, and are described elsewhere herein (see, e.g., the mouse assay models provided in the Examples). Insulinotropic peptides contemplated herein include GLP-1 (7-36), exendin-4, and derivatives thereof, including the specific derivatives disclosed elsewhere herein.

In one aspect of the invention, the derivatives of exendin-4 contemplated have amino acid sequences of the general formula: His-Gly-Glu-Gly-Thr-Phe-Thr-Ser-Asp-Leu-Ser-Lys-Gln-Xaa-Glu-Glu-Glu-Ala-Val-Yaa-Leu-Phe-Ile-Glu-Trp-Leu-Lys-Asn-Gly-Gly-Pro-Ser-Ser-Gly-Ala-Pro-Pro-Pro-Ser-Zaa (SEQ ID NO:2). In this formula, Xaa (at position 14 relative to the N-terminus) represents Arg, Leu, Ile or Met; Yaa (at position 20 relative to the N-terminus) represents His, Arg or Lys; Zaa (at position 40 relative to the N-terminus) represents Arg-OH, —OH, —NH$_2$ or Lys-OH. In this formula, when Xaa is Met and Yaa is Arg, Zaa cannot be —NH$_2$.

In the present invention, exendin-4 derivatives are generally referred to either by SEQ ID NO, or, alternatively, by following the name "exendin-4" with a designation within parentheses of each changed amino acid position in the sequence, where the new amino acid(s) at each changed position is/are given, followed by a subscript indicating the position of the change(s) relative to the N-terminal amino acid of the peptide. Thus, in this alternative nomenclature, SEQ ID NO:2 may also be designated as exendin-4 ((Arg/Leu/Ile/Met)$_{14}$, (His/Arg/Lys)$_{20}$, (Arg-OH/—OH/—NH$_2$/Lys-OH)$_{40}$).

Other exendin-4 derivatives specifically contemplated herein include, e.g.: exendin-4 ((Ile/Leu/Met)$_{14}$, (His/Lys)$_{20}$, Arg$_{40}$) (SEQ ID NO:3); exendin-4 ((not Lys/not Arg)$_{12}$, (not Lys/not Arg)$_{20}$, (not Lys/not Arg)$_{27}$, Arg$_{40}$) (SEQ ID NO:4); and exendin-4 ((not Lys/not Arg)$_{20}$, Arg$_{40}$) (SEQ ID NO:5).

Of particular interest are those exendin-4 derivative sequences of the present invention that are explicitly shown in the Examples below to possess exendin-4-like activity, i.e.: exendin-4 (Lys$_{20}$, Arg$_{40}$) (SEQ ID NO:6); exendin-4 (His$_{20}$, Arg$_{40}$) (SEQ ID NO: 7); and, exendin-4 (Leu$_{14}$, Lys$_{20}$, Arg$_{40}$) (SEQ ID NO:8). FIG. 1 provides an alignment of these sequences with both the wild-type exendin-4 amino acid sequence (SEQ ID NO:1) and with the wild-type GLP-1 (7-36) sequence (SEQ ID NO:9). In FIG. 1, underlining indicates changed or added amino acids relative to the wild-type exendin-4 sequence; shading represents amino acids that are present in corresponding positions in both the exendin-4 and GLP-1 (7-36) sequences; and, standard single letter abbreviations are used for the amino acids in accordance with the IUPAC-IUB Commission on Biochemical Nomenclature. Thus in FIG. 1, A corresponds to Ala; C corresponds to Cys; D corresponds to Asp; E corresponds to Glu; F corresponds to Phe; G corresponds to Gly; H corresponds to His; I corresponds to Ile; K corresponds to Lys; L corresponds to Leu; M corresponds to Met; P corresponds to Pro, Q corresponds to Gln; R corresponds to Arg; S corresponds to Ser; T corresponds to Thr; V corresponds to Val; W corresponds to Trp; and Y corresponds to Tyr.

The exendin-4 peptide derivatives of this invention are amphoteric (synonymous with amphiprotic) compounds, and may be sufficiently acidic or sufficiently basic to react with any of a number of inorganic bases, and inorganic and organic acids, to produce an exendin-4 derivative in salt form. Acids commonly employed to form acid-addition salts derivatives of the present invention are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesutfonate, propanesulfonate, naphthalene-1-sulfonate, naphthalene-2-sulfonate, mandelate, and the like. Preferred acid addition salts are those formed with mineral acids such as hydrochloric acid and hydrobromic acid, and, especially, hydrochloric acid.

Alkalis may also be employed to react with derivatives of this invention to form salts. Representative examples of such alkalis include ammonium, alkali metals, alkali metal hydroxides, carbonates, and bicarbonates. Typically, such an alkali may be sodium hydroxide, potassium hydroxide, ammonium hydroxide, and potassium carbonate.

Finally, other reactions or modifications to the exendin-4 derivatives of the invention may be performed to produce pharmaceutical compositions, as described in a separate section below.

General Methods for the Production of Exendin-4 Derivatives

One aspect of the present invention provides a method to produce an insulinotropic peptide or derivative thereof by solid phase synthesis, comprising using HMP resin as a solid phase carrier, protecting the alpha-amine of a residue with 9-fluorenyl methoxycarbonyl (Fmoc), synthesizing a residue on a peptide synthesizer by the amino acid sequence of an insulinotropic peptide derivative, and obtaining products after separation, purification and lyophilization. For example, the exendin-4 derivative peptides of the present invention may be synthesized by such chemical methods.

In another aspect, the present invention provides methods to produce an insulinotropic peptide derivative by recombinant techniques. One such recombinant technique contemplated herein comprises: synthesizing gene fragments of the amino acid sequence of an insulinotropic peptide derivative, e.g., an exendin-4 derivative; ligating the synthesized gene fragments; constructing a recombinant plasmid, culturing suitable bacterial host cells and transforming the recombinant plasmid into the bacterial host cells; extracting the inclusion bodies after fermentation of the bacteria strain and collapse of cell walls; and, obtaining the final product after lysing the inclusion bodies, separating rough product followed by HPLC purification and lyophilization. Although the desired exendin-4 or exendin-4 derivative gene of interest in this technique is indicated as being produced via synthetically generated DNA fragments, also contemplated herein are any suitable method for producing the gene of interest, e.g., by mutagenesis of the wild-type exendin-4 gene, by PCR methods, or by any other method known to the skilled artisan. Such techniques are intended to be generally applicable throughout the invention for the construction of the desired genes of the invention.

In an additional embodiment, the present invention is drawn to the production by recombinant techniques of multimeric fusion proteins of the exendin-4 peptide derivatives of interest, specifically tandemly linked multimers of the exendin-4 sequence, derivatives of the exendin-4 sequence, or some combination thereof. These techniques are contemplated as comprising: constructing an expression vector comprising at least two tandemly linked exendin-4 DNA sequences or derivatives thereof and a promoter sequence, wherein the promoter sequence is capable of driving the expression of the tandemly linked exendin-4 DNA sequences or derivatives thereof; expressing the expression vector in a host cell to produce a fusion protein comprising at least two tandemly linked exendin-4 peptide sequences or derivatives thereof; and, cleaving the resulting fusion protein into separate exendin-4 peptides or derivatives thereof.

In the production of such fusion proteins by recombinant techniques, the exendin-4 sequences or derivatives are tandemly linked. "Tandemly linked" or "tandem linkage" as used herein to refer to the peptides of the invention indicates any linkage between the peptides of interest that allows for the production of a single fusion protein that may be cleaved by the appropriate cleavage reagent to produce separate peptides of the desired sequence.

Thus a tandem linkage between two exendin-4 peptide derivative sequences comprises a "specifically cleavable peptide bond," i.e., a peptide bond that can be specifically recognized and cleaved by the appropriate cleavage reagent. The amino acid residue at which the actual rupture of the peptide bond occurs is designated herein as a bond-forming amino acid ("BFAA"). Some examples of BFAA contemplated herein include: Met, which may be recognized by the cleavage reagent cyanogen bromide ("CNBr"); Arg or Lys, which may be recognized by alkaline protease cleavage reagents such as trypsin; the amino acid sequence Asp-Asp-Asp-Asp-Lys (SEQ ID NO:26), which may be recognized by the cleavage reagent enterokinase; and, other proteases such as clostripain.

In the present invention "tandemly linked" or "tandem linkage" is also used to refer to the joining of DNA sequences of the invention. In this context, "tandemly linked" DNA sequences are DNA sequences that are so joined that they serve as the template for the production by transcription/translation of a tandemly linked fusion peptide, e.g., two copies of the DNA sequences corresponding to any of SEQ ID NOS:3 and 5-8 or combination thereof.

Thus in one embodiment of the present invention, two or more exendin-4 or exendin-4 peptide derivative sequences (or some combination thereof) may be tandemly linked without any intervening amino acid sequence, i.e., without a spacer sequence. As an example, two exendin-4 derivative sequences in which an Arg residue has been added to the C-terminus (e.g., two copies of any of SEQ ID NOS:3 and 5-8 or combination thereof) may be tandemly linked such that the Arg at the C-terminus of the first exendin-4 derivative sequence is immediately followed by the His at the N-terminus of the next (i.e., tandemly linked) exendin-4 derivative sequence. Similar tandem linkage of more copies of such exendin-4 derivative sequences allow for the production of a fusion protein in which N copies of the exendin-4 sequence are repeated. In these constructs, treatment with, e.g., trypsin, will cleave the fusion protein after each C-terminal Arg residue to produce separate exendin-4 derivative sequences.

In another embodiment, exendin-4 or exendin-4 derivative sequences may be tandemly linked with an amino acid spacer of Xaa . . . Xaa between the C-terminus of one peptide and the N-terminus of the next peptide in the fusion protein. "N-terminal cleavage" within this spacer will produce peptides in which the exendin-4 or exendin-4 derivative sequence contains additional spacer amino acids at the C-terminus (i.e., a "C-terminal tail"), while "C-terminal cleavage" within this spacer will produce peptides in which the exendin-4 or exendin-4 derivative sequence contains additional spacer amino acids at the N-terminus (i.e., an "N-terminal leader"). The present invention contemplates situations in which both N- and C-terminal cleavages will be performed to yield peptide sequences lacking any spacer amino acids. The present invention also contemplates situations in which only an N-terminal cleavage or only a C-terminal cleavage is performed, thereby producing the desired exendin-4 or exendin-4 derivative sequence with either an N-terminal leader or C-terminal tail.

In forming the fusion peptides described above, it is necessary to form a DNA construct capable of being transcribed/translated to produce the desired fusion peptide. When a fusion peptide lacking a spacer amino acid sequence is to be produced, one of ordinary skill would understand to use DNA methods for producing a construct encoding a peptide lacking a spacer. i.e., a construct where the triplet nucleotide codon for the C-terminal amino acid of the first exendin-4 peptide derivative is immediately followed by the triplet nucleotide codon for the N-terminal amino acid of the following exendin-4 peptide derivative. Alternatively, when a fusion peptide containing a spacer is desired, appropriate techniques such as the "hybrid site" technique discussed elsewhere herein may be used to construct a DNA sequence where the triplet nucleotide codon for the C-terminal amino acid of the first exendin-4 peptide derivative is followed by the appropriate number of in-frame triplet nucleotide codons for the amino acid spacer, and then by the triplet nucleotide codon for the N-terminal amino acid of the following exendin-4 peptide derivative.

In order for the fusion proteins containing tandemly linked exendin-4 sequences or derivatives thereof to be correctly cleaved to produce separate peptides of the desired sequence, it is necessary that cleavage does not occur within these sequences. For example, the use of trypsin as a cleavage reagent will result in cleavage at any of the internal $Lys_{12}$, $Arg_{20}$, and $Lys_{27}$ amino acid residues of the wild-type exendin-4 sequence that are present in the fusion protein. Thus in instances where the cleavage reagent has an internal recognition site or sites within the exendin-4 sequences or derivatives thereof of the fusion protein, it will be necessary to alter these sequences to remove these internal cleavage sites.

In the present invention, "removal" of an internal cleavage site is contemplated to include changes in the sequence itself that remove a site. Such "removal" of an internal site is also contemplated to include chemical modifications of the sequence that "remove" (i.e., protect) an amino acid from cleavage.

Thus one form of alteration contemplated to remove an internal cleavage site involves the alteration of the internal site(s) by substitution of the amino acid or acids that serve as the site(s). For example, when trypsin is used as the cleavage reagent, one method of preventing cleavage at the internal $Lys_{12}$, $Arg_{20}$, and $Lys_{27}$ residues of the exendin-4 sequence is to "remove" these residues and replace them with residues that are not recognized for cleavage by trypsin, i.e., by residues that are neither Arg nor Lys. See, e.g., the peptide sequence of SEQ ID NO:4. Such replacement amino acids may be any amino acid, including derivatized or uncommon amino acids such as are well known to the skilled artisan. One criterion for the selection of such replacement amino acids is that their substitution into the exendin-4 derivative sequence not abolish the exendin-4-like activity of these exendin-4 derivative sequences, with assays for measuring this activity described elsewhere herein. In the context of preserved exendin-4-like activity, conservative or highly-conservative amino acid substitutions are preferred.

In a related embodiment, the invention contemplates alterations of the exendin-4 derivative sequence where the cleavage site is "removed" by alteration of secondary residues around the site, i.e., residues that, while not directly involved in the recognition of the site by the cleavage reagent may still affect cleavage when they are altered. When the cleavage reagent is trypsin, for example, substitution of a Pro adjacent to, and downstream (i.e. towards the C-terminus of the peptide) from the Arg or Lys residue that constitutes the trypsin cleavage site will inhibit trypsin cleavage after the Arg or Lys residue.

In making such substitutions to the exendin-4 sequence to remove internal cleavage sites, it is generally preferable to maintain the activity of the exendin-4 derivatives produced by such substitutions. Such conservation of activity may be made based on predictions as to appropriate substitute amino acid residues, for example based on conservative or highly conservative amino acid substitutions such as the substitution of Arg with His or Lys. Predictions of appropriate amino acid substitutions may also be made based on data regarding sequence conservation at particular amino acid positions, e.g., data such as the comparison of the sequences of exendin-4 and GLP-1 (7-36) shown in FIG. 1.

Alternatively, substitutions that maintain the activity of the exendin-4 derivatives produced by such substitutions may be identified by the screening of exendin-4 derivatives for exendin-4-like activity. Specifically, random or directed mutations in the exendin-4 sequence produced by standard means may be screened for their effect on the activity of the resulting exendin-4 derivative peptide by activity assays appropriate for exendin-4.

An alternative method of altering the exendin-4 derivatives of the present invention to "remove" internal cleavage sites involves the use of reversible chemical modification of those sites. With regard to trypsin cleavage, for example, reversible acetylation methods may be used to protect internal Lys residues by chemical modification, thereby removing them as trypsin cleavage sites. In this situation, any internal Arg residues (e.g., the exendin-4 $Arg_{20}$) must be "removed" by the previously discussed method of amino acid replacement (since only the Lys residues are "removed" by acetylation), and an Arg added as a cleavage site between the tandemly linked exendin-4 derivative sequences. Examples of sequences contemplated for such acetylation modification prior to trypsin cleavage include those presented in SEQ ID NOS:3 and 5-8.

Reversible acetylation methods to protect internal Lys residues include methods involving the use of an acetylating agent such as succinyl anhydride or derivatives thereof; other anhydrides such as acetic anhydride, citraconic anhydride, or 3,4,5,6-tetrahydophthaloyl anhydride; or other compounds such as would be known to one of ordinary skill in the art to be capable of acetylating the $\epsilon$-$NH_2$ in the Lys residue(s). Such acetylation is conducted by, e.g., suspending the purified wet inclusion body in a $Na_2CO_3$ solution, and then gradually adding the acetylating agent to the solution with stirring at room temperature at pH 8. After 4 hours, the reaction mixture is dialyzed overnight in phosphate buffer, and the fusion protein in the dialyzed reaction mixture is digested with trypsin at a ratio of protein-to-trypsin of about 1000:0.5-2 (w/w) at 30° C. for 2 hours. During the reaction, digestion is monitored by HPLC analysis.

In order to remove protecting acetyl groups, after digestion, the acyl group from the $\epsilon$-$NH_2$ is deprotected under standard conditions, e.g., by acidifying the reaction mixture for 4-6 hours at room temperature using HCl to a pH of about pH 2-3, followed by neutralization (e.g., with $NaHCO_3$ to pH 5.0). The resulting precipitate is then centrifuged, and the crude exendin-4 derivative is collected from the precipitate.

As discussed previously, the exendin-4 derivatives of the invention are contemplated to include exendin-4 peptides which have multiple changes. For example, an exendin-4 derivative which lacks any internal trypsin cleavage sites may be further derivatized by additional amino acid substitutions and/or additions. Thus one aspect of the invention is directed to exendin-4 peptide derivative lacking an internal cleavage site or sites for the cleavage reagent of interest, where such an exendin-4 peptide derivative has further amino acid changes that, in total, preserve a % similarity between the exendin-4 derivative sequence and the wild-type exendin-4 sequence of at least 85%, 86%, 87%, 88%, 89%, 90%, 91%, 93%, 93%, 94%, 95%, 96%, 97%, 98%, or 99%, and that do not eliminate the exendin-4-like activity of the derivative sequence. For example, derivatives may include sequences in which, in addition to removal of the internal cleavage sites of the cleavage reagent, have 1, 2, 3, 4, 5, 6, 7, 8, 9, or 10 additional amino acid changes (i.e., changes not related to the removal of the cleavage site or sites) and that still retain exendin-4-like activity. Such small changes in sequence would be well-known to one of ordinary skill in the art. Examples of such changes may be found in the relevant literature for insulinotropic peptides. Methods for the calculation of % similarity are well-known to one of ordinary skill in the art.

Also contemplated as included within the term "exendin-4 derivatives" are exendin-4 derivative sequences that are further modified by any of the modifications known to the skilled artisan, particularly those modifications that improve the properties of the exendin-4 derivative, e.g., the half-life of the peptide. For example, U.S. Pat. No. 6,593,295, herein incorporated by reference, discloses side-chain modifications to the peptide sequence that may be applied to any of the exendin-4 derivatives contemplated herein.

Similarly, U.S. Pat. No. 6,528,486, herein incorporated by reference and its corresponding international application WO 01/04156 refer to a variety of modifications that are also intended to be encompassed within the present invention, including the modification of the C-terminus of the peptide by the addition of one or more lysine residues. Thus the exendin-4 derivatives of the present invention may be modified at the C-terminus, e.g., the C-terminal -Gly-Ala-Pro-Pro-Pro-Ser sequence (SEQ ID NO:22) may be modified to -Gly-Ala-Pro-Lys$_n$-Arg (SEQ ID NO:23), -Gly-Ala-Ser-Lys$_n$-Arg (SEQ ID NO:24), -Gly-Ala-Lys$_n$-Arg (SEQ ID NO:25), etc., where n is an integer from 1-10, preferable with a value of 6.

As contemplated herein, "exendin-4 derivatives" also encompasses wild-type exendin-4 sequences (e.g., two copies of the DNA sequences corresponding to any of SEQ ID NOS:3 and 5-8 or combination thereof) where modification are made not to the amino acid sequences itself, but to the side chains of the amino acids, i.e., by cross-linking of reagents known to one of ordinary skill in the art, etc.

"Hybrid-Site" Methods for the Production of Exendin-4 Derivatives

In one aspect of the invention, exendin-4 peptide derivatives may be produced by "hybrid-site" techniques, where appropriate restriction site combinations are used to generate the vectors that direct the expression of the exendin-4 peptide derivative, either as a monomer, or as a multimeric fusion protein. Although the use of such restriction sites as a means of generating these vectors are specific to this section, the other aspects of the invention described in this section are intended as generally applicable throughout the present application.

Thus one embodiment of the invention is directed to a technique for producing exendin-4 derivatives which comprises the steps of: introducing individually two restriction endonucleases cleavage sites capable of forming a hybrid site to the 5' and 3' ends of the gene encoding the exendin-4 peptide derivative; ligating the cohesive ends to form a hybrid site after digesting with restriction endonucleases, cloning into a vector N tandemly linked exendin-4 peptide derivative genes, wherein N is an integer from 1 to 32; transforming the vector so obtained into a host cell; expressing in the host cell a fusion protein containing N exendin-4 peptide derivatives, where N is an integer from 1 to 32; cleaving the fusion protein; and, separating and purifying the exendin-4 peptide derivative molecules so obtained.

The two restriction endonucleases which may be used to form a "hybrid site" include, but are not limited to, BglII and BamHI, SalI and XhoI. For example, the base sequence recognized by BglII is A|GATCT, while the sequence recognized by BamHI is G|GATCC. After digesting the two sequences with corresponding restriction enzymes, ligation of the resulted complementary cohesive ends will form a sequence of AGATCC or GGATCT, which cannot be cut by either BglII or BamHI. Such a sequence is called a "hybrid site," and may be used to ligate multiple copies of the relevant gene(s) in tandem.

The exendin-4 derivative genes for use in this technique (or in the other techniques of the invention) may be generated in several ways, including ligating several synthetic fragments by cohesive ends or blunt ends to generate the target gene, or by synthesizing the whole target gene by chemical synthesis. Preferably, codons with high frequency in E. Coli are used to synthesize the appropriate gene fragments.

In one embodiment of the "hybrid site" method, the exendin-4 peptide derivative gene is constructed so as to have BglII and BamHI at its ends. These sites are required to link these genes in tandem. The cloning sites of EcoRI and HindIII are required for insertion into a vector. The positions for the BglII and BamHI recognition sites may be exchanged.

In another embodiment of the "hybrid site" method, present invention, the exendin-4 peptide derivative gene is constructed so as to have SalI and XhoI at its ends. The cloning sites of EcoRI and HindIII are required for insertion into a vector.

Multiple copies of genes encoding an exendin-4 peptide derivative can be tandemly linked using the above-mentioned endonuclease sites, and then can be cloned into a vector. These genes linked in tandem can also be mixed-and-matched, that is, genes encoding different exendin-4 peptide derivatives may be tandemly linked, thereby producing a fusion protein that, when cleaved by the appropriate cleavage reagent, will produce a heterogeneous mixture of exendin-4 derivatives. Such a heterogeneous mixture of exendin-4 peptide derivative sequences may have greater pharmaceutical utility as compared to a homogenous population of exendin-4 peptide derivatives.

Vectors suitable for the present invention may be chromosome-derived, non-chromosome-derived, or synthetic. These vectors may include, but are not limited to, microphage DNA, bacillus virus, bacterial plasmid, yeast plasmid, and vectors derived from a combination of phage, plasmid and viral DNA. The viral DNA may include, but is not limited to, bovine and poultry small pox virus, adenovirus, and pseudorabies virus. Many other suitable vectors are well known to one skilled in the art. Any plasmid or vector that exist and replicates stably in host cells may be used in this invention.

Representative but non-limiting examples of the expression vectors contemplated in the present invention include those used in bacterial systems, such as commercially available plasmids pKK233-2, pKK223-3, pEZZ18, pUC18, pUC19, and pT7 (Amersham Pharmacia Biotech).

In the present invention the target gene is linked to an appropriate promoter on an expression vector. A promoter is a sequence that can regulate and control gene transcription, i.e., is capable of driving the expression of a protein sequence using a DNA template. The representative examples of promoter include lac, trp, tac of E. Coli; T7 of phage; $P_L$ of λ phage, and other known promoters existing in prokaryotic cells, eukaryotic cells, and viruses that control gene expression. Particularly preferred bacterial promoters include lacI, lacZ, T3, T7, Protein A signal peptide, gpt, $\lambda P_R$, $P_L$ and trp. The selection of appropriate promoters is apparent to one skilled in the art.

In addition, the preferred expression vector may have one or more selection marker gene(s) in order to facilitate screening of the host cells. Such marker genes include tetracycline and penicillin resistance genes in *E. Coli*, and dihydrofolate reductase and neomycin resistance genes in eukaryotic expression systems.

The expression vectors of the present invention may contain N copies of the exendin-4 peptide derivative gene linked in tandem. Preferably, N is an integer from 1 to 32. more preferably N is an integer from 8 to 32, and still more preferably N is either 16 or 32. Thus the present invention encompasses expression vectors containing 1, 2, 4, 8, 12, 16, 32, or more tandemly linked exendin-4 peptide derivative genes.

The vectors of the present invention are transformed into appropriate host cells to express the fusion proteins in the host cells. The expression vector can be introduced into host cells by any standard method as would be known to one of ordinary skill in the art, e.g., by transformation, transfection, or infection. For example, the expression vector may be introduced via transformation with calcium chloride, transfection in the presence of DHAE-dextran as a carrier, or by electroperforation. These methods will efficiently transfer the vector containing multiple copies of gene(s) of the present invention into host cells. The vectors referred to herein can be plasmids, viral particles, or bacterial phages.

Suitable host cells may include, but are not limited to, bacterial cells such as *E. Coli*, streptococcus, salmonella, and eukaryotic cells such as yeast. The selection of the appropriate host cells is apparent to one skilled in the art. For the purpose of lowering production costs, prokaryotic cells are the preferred host cells. Representative examples include a variety of strains of *E. coli*, e.g., JM103, JM109, HB101, and DH5α.

The host cells of the present invention contain an expression vector containing N copies of the exendin-4 peptide derivative gene. Consequently, the fusion proteins expressed by these host cells will contain N tandemly linked copies of the exendin-4 peptide derivative.

The genetically engineered bacterial strains of the present invention are cultured under appropriate conditions to produce and accumulate fusion proteins composed of N copies of the linked polypeptides. The culturing conditions such as culturing media, temperature, humidity and pH value are apparent to one skilled in the art.

After the host cells have grown to a proper density, they can be harvested, e.g., by centrifugation. The harvested cells are then ruptured by physical or chemical methods, and the resulting product is collected and subject to further purification.

The host cells expressing recombinant proteins can be ruptured by any conventional means, which may include, but are not limited to, freeze and thaw cycles, ultrasonic or mechanical treatment, or cellular lysis reagents. The selection of appropriate protocols to break up host cells is apparent to one skilled in the art.

After rupture of host cells, inclusion bodies are obtained, as described in the experimental protocol of Example 11.

In those aspects of the present invention in which exendin-4 peptide derivative fusion proteins are produced, the peptides obtained in the inclusion bodies must be cleaved with the appropriate cleavage reagent. Examples of cleavage with clostripain and trypsin are provided in Example 12.

After fusion protein cleavage, highly purified polypeptide can be obtained via a series of separation and purification steps, e.g., by chromatographic methods. Such chromatographic methods may include, but are not limited to, ion-exchange, hydrophobic, size exclusion, and reverse phase chromatography. The media used in these methods may be purchased from commercial vendors, such as Amersham Pharmacia Biotech, Whatman, Merk KgaA, and Grace Vydac etc. Single chromatography or a combination of multiple chromatography steps may also be used in the purification processes. In general, HPLC is used as a means of purification. Typically, C18 reversed phase chromatography with a TFA-$CH_3CN$ system as mobile phase is utilized. These chromatographic methods are well known to one skilled in the art.

Pharmaceutical Compositions

The insulinotrophic peptides of the present invention can be incorporated into pharmaceutical compositions. Such compositions typically include the insulinotrophic peptide (synonymously, "active compound" and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions, including various different insulinotrophic peptides of the present invention.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral, buccal, parenteral or inhalation compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and thereby reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein or polypeptide can include a single treatment or, preferably, can include a series of treatments.

The present invention is further illustrated by the following examples, which should not be construed as limiting, but are merely exemplary in nature. The contents of all references, patents and published patent applications cited throughout this application are incorporated herein by reference.

EXAMPLES

Example 1

Preparation of the Exendin-4 Derivative Exendin-4 (His$_{20}$, Arg$_{40}$) by Solid Phase Synthesis A. Amino Acid Monomers.

The following amino acid monomers were used:

Fmoc-L-Ala-OH
Fmoc-L-Asn(Trt)-OH
Fmoc-L-Asp(OtBu)-OH
Fmoc-L-Gln(Trt)-OH
Fmoc-L-Glu(OtBu)-OH
Fmoc-L-Gly-OH
Fmoc-L-His(Trt)-OH
Fmoc-L-Ile-OH
Fmoc-L-Leu-OH
Fmoc-L-Lys(Boc)-OH
Fmoc-L-Met-OH
Fmoc-L-Phe-OH
Fmoc-L-Pro-OH
Fmoc-L-Ser(tBu)-OH
Fmoc-L-Thr(tBu)-OH
Fmoc-L-Trp-OH
Fmoc-L-Tyr(tBu)-OH
Fmoc-L-Val-OH In this table, Fmoc refers to 9-fluorenyl methoxycarbonyl; BOC refers to tert-butyloxycarbonyl; Trt refers to trityl; OtBu refers to tertiary butyl ester; and tBu refers to tert-butyl.

B. Apparatus and Reagents.

Peptide syntheses were conducted using a model 433A peptide synthesizer (Applied Biosystems, USA). Reagents used for these synthese were: N-methyl ketopyrrolidine, methylene chloride, hexahydropyridine, methanol, dimethylaminopyridine/DMF N,N-diisopropylethylamine/NMP, 100 mmole HBTU/0.5 M HOBT in DMF, N,N-Dicyclohexylcarbodiimide/NMP, where DMF refers to N,N-Dimethylformamide; NMP refers to N-methylpyrrolidone; HOBT refers to 1-Hydroxybenzotriazole; and HBTU refers to 2-(1H-benzotriazole-yl-1,1,3,3-tetramethyl-Uronium hexafluorophosphate).

C. Procedure.

C1. Synthesis.

For, e.g., a 0.25 synthesis scale, 0.25 g of HMP resin was weighed and placed in the synthesizer's reactor vessel. 1 mmol of various residues, each coupled with protecting groups, were weighed and arrayed in the synthesizer by the amino acid sequence of the insulinotropic peptide derivative from the carboxy terminal to the amino terminal. At a room temperature of 25° C., reactions for removing Fmoc protection, activating a residue and attaching the activated residue to HMP resin were automatically performed under the control of a computer program. Such reactions were repeated until the whole peptide was synthesized. After completion of the synthesis, the residue-attached resin, with each residue coupled with side-chain-protecting groups, was air dried on a peptide synthesizer and then weighed.

C2. Removal of Protecting Groups and Detachment of Resin.

The residue-attached resin with each residue of the insulinotropic peptide derivative coupled with protecting groups was placed in a plugged ehrlenmeyer flask, and cleavage reagents were added as shown below.

| Reagent | Dosage |
| --- | --- |
| Water | 0.50 ml |
| methyl phenate | 0.50 ml |
| Phenol | 0.75 g |
| Mercaptoethanol | 0.20 ml |
| trifluoroacetic acid | 10.0 ml |

This reaction was carried out at constant temperature of 30° C. for 6 hours with constant stirring. After filtrations, the aqueous filtrate was collected, the resin was washed with a small amount of trifluoroacetic acid, the collected aqueous filtrate and the washing solution were mixed together, and ether was added for precipitation. The mixture was filtered, and the resulted precipitate was washed with small amount of ether. After evaporation in a vacuum evaporator, the crude product was obtained.

C3. Purification by HPLC and Lyophilization.

Separation and purification of the crude product was achieved by using preparative HPLC. Final product was obtained after lyophilization. The molecular weight of the product was confirmed using chromatogram-mass spectrogram joint analysis (data not shown).

Example 2

Preparation of the Exendin-4 Derivative Exendin-4 (Leu$_{14}$, Lys$_{20}$, Arg$_{40}$) by Bio-engineering Techniques A. Synthesis of Gene Fragments.

Gene fragments 10-13 were synthesized based on the amino acid sequence of the insulinotropic peptide derivative exendin-4 (Leu$_{14}$, Lys$_{20}$, Arg$_{40}$) (SEQ ID NO:8). In these sequences, fragment 4 (SEQ ID NO:13) is the inverse complement of fragment 1 (SEQ ID NO:10), and fragment 3 (SEQ ID NO:12) is the inverse complement of fragment 2 (SEQ ID NO:11). When these fragments are annealed and ligated they produce the DNA sequence of the top panel of FIG. 5 (SEQ ID NO:15), as well as the inverse complement of this sequence.

B. Cloning

B1. Ligation.

Two tubes were taken, and fragments 1 and 4 with their OD$_{260\ nm}$=0.1 (optical density at 260 nm) were drawn into one tube, while fragments 2 and 3 with the same optical density were drawn into the other tube. Then polynucleotide kinase buffer, polynucleotide kinase and ATPs were added to the two tubes respectively. The reaction mixtures were incubated at 37° C. for 60 minutes to make the 5' terminal of the gene fragment phosphorylated. Then the two tubes were placed in a water bath of 95° C. and were incubated for 10 minutes. The water bath was stopped to warm up and was naturally cooled down to room temperature, while annealing reaction was carried out during the process. T4 ligase and T4 ligase buffer were added to the two tubes respectively, and the mixtures were incubated overnight at 16° C. for ligation of gene fragments.

B2. Plasmid.

A plasmid containing a promotor such as Lac, $P_L$ or Tac was drawn in a tube and digested with restriction endonucleases EcoRI and HindIII. The digested plasmid was extracted with hydroxybenzene:chloroform solvent and collected by centrifugation. The aqueous phase was remained and washed three times with chloroform solvent. Centrifugation was continued, and the resulted aqueous phase was precipitated with isopropanol solvent, followed by centrifugation and an air-dry step.

The digested plasmid and the ligated fragment were mixed together. T4 ligase and ligase buffer were added to the mixture. Ligation reaction was carried out at room temperature for 3-4 hours.

B3. Culturing of Host Cells.

Bacterial cells of *E. coli* JM103 were incubated with shaking at 37° C. in LB liquid medium (1000 ml of LB liquid media containing 10 g of peptone, 5 g of yeast extract, and 10 g of NaCl) for 4 hours. After the bacterial cultures were centrifuged, the collected bacterial cells were treated with calcium chloride solution and kept at −4° C. for further use.

B4. Transformation.

The cloned plasmid was transformed into *E. coli* JM103 host cells. The transformed bacterial cells were incubated in an ice bath for 30 minutes, and then incubated at 42° C. for 2 minutes. Bacterial cells were spread on an agar plate containing ampicillin, and were incubated overnight at 37° C. Colony screening was then conducted, and those colonies containing recombinant plasmids were retained for further use.

B5. Fermentation.

A screened colony harboring a recombinant plasmid carrying the derivative gene was incubated with shaking in LB liquid medium. 0.5 mM of Isopropyl beta-D-Thiogalactopyranoside (IPTG) was added for the purpose of protein induction. Bacterial cells were incubated overnight and harvested by centrifugation. The expressed protein was identified by polyacrylamide gel electrophoresis (PAGE) containing 12% sodium dodecanesulphonate.

C. Inclusion Bodies.

Ten bottles, each containing 300 ml of bacterial cultures, were incubated with shaking under the conditions described above. After protein induction, lysis solution (20 mM phosphonic acid buffer containing 1% sodium chloride, pH 7.5) and lysozyme were added. The bacterial cultures were incubation at 30° C. for 30 minutes and then centrifuged. The collected precipitate was treated with 6 M guanidine hydrochloride (GuHCl) for extraction of inclusion bodies, centrifuged, and the resulting supernatant was dialyzed to remove GuHCl. The dialysate was washed three times with 20 mM phosphonic acid buffer (containing 1% sodium chloride and 0.1% Tween 80, pH 7.5), and inclusion bodies were obtained thereafter.

D. Lysis.

The inclusion bodies were dissolved in 8 M urea solution. Hydrochloric acid was added to a concentration of 50 mM. After addition of CNBr, the solution was stirred in the dark under nitrogen for 2 hours, followed by HPLC analysis.

E. Purification.

After completion of the CNBr lysis reaction, crude product was obtained through partition chromatography on Sephadex G-25, and final product was thereafter obtained by HPLC. Similar to the result of solid phase synthesis, it was shown by mass spectrum analysis that the determined molecular weight of the peptide derivative is consistent with the theoretical weight (data not shown).

Example 3

The Exendin-4 Derivatives Exendin-4 ($Leu_{14}$, $Lys_{20}$, $Arg_{40}$), Exendin-4 ($Lys_{20}$, $Arg_{40}$), and Exendin-4 ($His_{20}$, $Arg_{40}$) Retain the Activity of Exendin-4 of Buffering Blood Glucose Levels in C57 BL/6J Mice After Glucose Challenge Experiments were conducted to determine the effect on the blood glucose levels of non-diabetic C57 BL/6J mice of the exendin-4 ($Leu_{14}$, $Lys_{20}$, $Arg_{40}$) peptide derivative relative to GLP-1 and the wild-type exendin-4 peptide. Overnight-fasted C57 BL/6J mice weighing 20 g were injected with a 20% glucose solution (200 μl) intra-peritoneally and simultaneously subcutaneously injected with either a saline control, GLP-1 (1 μg), exendin-4 (0.2 μg), or exendin-4 ($Leu_{14}$, $Lys_{20}$, $Arg_{40}$) (0.2 μg). Blood glucose levels were determined using standard glucose determination kits at 0, 30, 60, and 120 minutes post-injection.

As FIG. 2 shows, injection of saline alone after glucose challenge (i.e., the control experiment) caused a rapid rise in blood glucose levels by 30 minutes post-injection, followed by a slow decline in glucose levels over the next 90 minutes. In contrast, wild-type exendin-4 peptide ("ex-4 wt") co-injected with the glucose challenge acted to buffer changes in blood glucose levels (i.e., to reduce changes in glucose levels away from the pre-glucose-challenge levels), as did co-injected GLP-1. Co-injection with the exendin-4 derivative exendin-4 ($Leu_{14}$, $Lys_{20}$, $Arg_{40}$) ("ex-4 m") produced a response profile virtually identical to that seen with the wild-type exendin-4 sequence, indicating that the amino acid changes at positions 14, 20, and 40 in the exendin-4 derivate relative to the wild-type exendin-4 do not significantly alter the exendin-4-like glucose buffering activity of the derivative peptide.

Similar results were also obtained in experiments involving the related exendin-4 derivative peptides exendin-4 ($Lys_{20}$, $Arg_{40}$) and exendin-4 ($His_{20}$, $Arg_{40}$) (data not shown).

Example 4

The Exendin-4 Derivatives Exendin-4 ($Leu_{14}$, $Lys_{20}$, $Arg_{40}$), Exendin-4 ($Lys_{20}$, $Arg_{40}$), and Exendin-4 ($His_{20}$, $Arg_{40}$) Retain the Activity of Exendin-4 of Buffering Blood Glucose Levels in db/db Diabetic Mice After Glucose Challenge In order to extend the experimental results obtained in Example 3 with non-diabetic mice, experiments were also conducted to determine the effect on blood glucose levels of db/db diabetic mice of the exendin-4 ($Leu_{14}$, $Lys_{20}$, $Arg_{40}$) peptide derivative relative to GLP-1 and Rapid Insulin.

Specifically, 2-hour-fasted db/db mice weighing 50 g were injected with a 20% glucose solution (200 μl) intra-peritoneally and simultaneously subcutaneously injected with either a saline control, GLP-1 (4 µg), exendin-4 (Leu$_{14}$, Lys$_{20}$, Arg$_{40}$) ("E4m")(0.2 µg), or the commercially available insulin, Humalog® (Eli Lilly and Company) (4 µg). Blood glucose levels were determined using standard glucose determination kits at 0, 30, 60, 120, and 180 minutes post-injection, and hypoglycemia (%) was calculated relative to the baseline (t=0) blood glucose level of animals receiving saline control.

Figure 3:
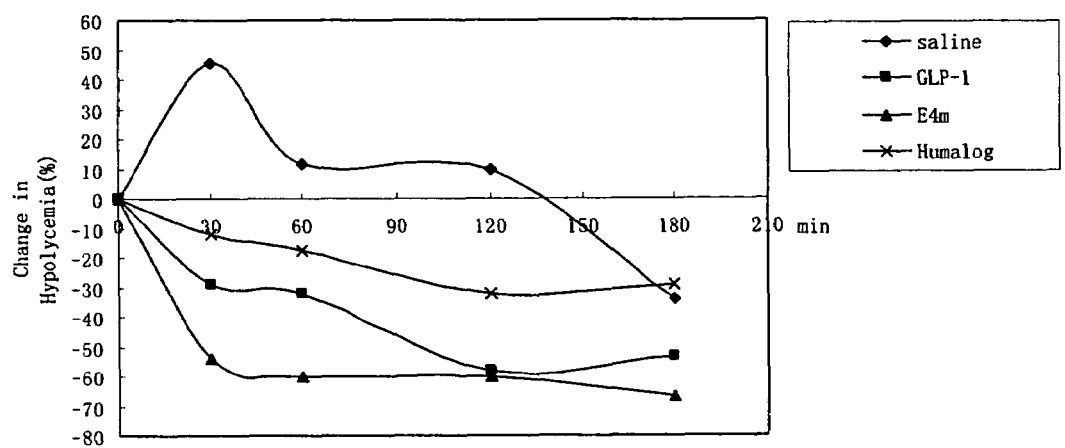
FIG. 3 shows the effects of saline control, GLP-1, the exendin-4 derivative exendin-4 (Leu$_{14}$, Lys$_{20}$, Arg$_{40}$) ("E4m") and the commercially available insulin Humalog® on the blood glucose levels of db/db diabetic mice after glucose challenge.

As FIG. 3 shows, injection of glucose only caused a rapid rise in blood glucose levels by 30 minutes post-injection, followed by a decline in glucose levels over the next 150 minutes. In contrast, co-injection of GLP-1 or Humalog® with the glucose challenge resulted in the buffering of changes in blood glucose levels, as did co-injection with the exendin-4 derivative peptide exendin-4 (Leu$_{14}$, Lys$_{20}$, Arg$_{40}$). These data further confirm the results of Example 3 demonstrating that the amino acid changes at positions 14, 20, and 40 in the exendin-4 (Leu$_{14}$, Lys$_{20}$, Arg$_{40}$) derivative peptide relative to the wild-type sequence do not significantly alter its exendin-4-like glucose buffering activity.

Similar results were also obtained in experiments involving the related exendin-4 derivative peptides exendin-4 (Lys$_{20}$, Arg$_{40}$) and exendin-4 (His$_{20}$, Arg$_{40}$) (data not shown).

Example 5

The Exendin-4 Derivative Exendin-4 (Leu$_{14}$, Lys$_{20}$, Arg$_{40}$) Retains the Activity of Exendin-4 of Buffering Blood Glucose Levels in C57 BL/6J Mice After a Second Glucose Challenge In order to determine the long-term ability of the exendin-4 derivative exendin-4 (Leu$_{14}$, Lys$_{20}$, Arg$_{40}$) to buffer blood glucose levels, experiments were performed in which blood glucose levels in the presence of this exendin-4 derivative were determined at various times after an initial glucose challenge at 0 minutes and then a second glucose challenge at 240 minutes.

Specifically, overnight-fasted C57 BL/6J mice weighing 20 g were injected with a 20% glucose solution (200 µl) intra-peritoneally and simultaneously subcutaneously injected with either a saline control, GLP-1 (1 µg), or exendin-4 (Leu$_{14}$, Lys$_{20}$, Arg$_{40}$) (0.2 µg). Then, at 240 minutes after the initial injection a second injection of 20% glucose solution (200 µl) intra-peritoneally was performed. Blood glucose levels were determined using standard glucose determination kits at 0, 30, 60, 240, 270, and 300 minutes after the first injection.

Figure 4:
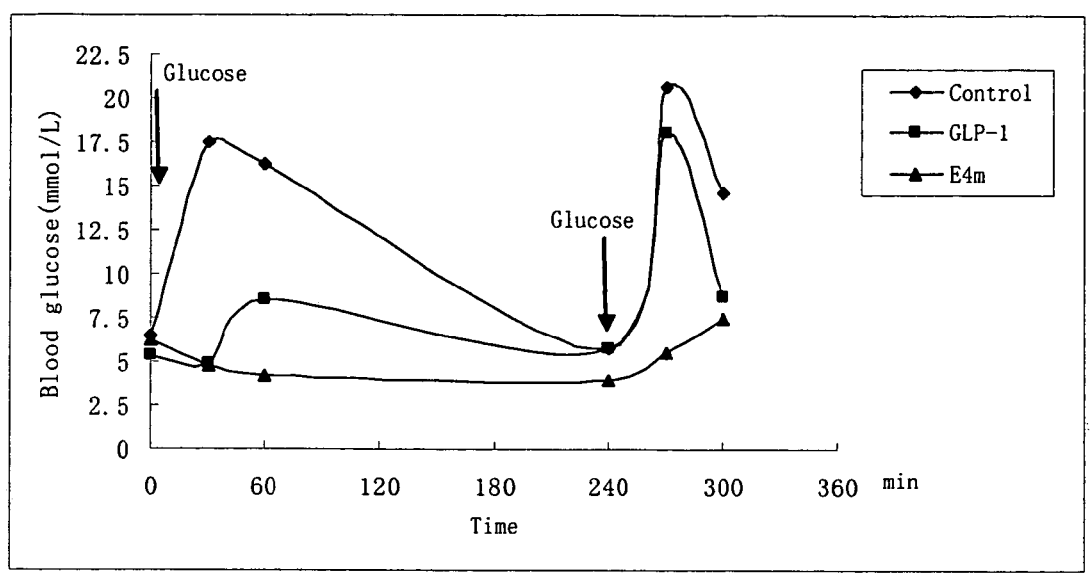
FIG. 4 shows the long-term hypoglycemic effects of control, GLP-1, and the exendin-4 derivative exendin-4 (Leu$_{14}$, Lys$_{20}$, Arg$_{40}$) ("E4m") on the blood glucose levels of non-diabetic C57 BL/6J mice after a second glucose challenge. Vertical arrows indicate times of administration of glucose challenges.

As FIG. 4 shows, the initial injection of glucose caused a rapid rise and then slow decline in blood glucose levels in the control experiment, an effect that was drastically reduced by the inclusion of GLP-1 in the initial injection, and that was essentially eliminated by the inclusion of exendin-4 (Leu$_{14}$, Lys$_{20}$, Arg$_{40}$) ("E4m") in the initial injection. FIG. 4 also shows that a second glucose challenge at 240 minutes after the first injection resulted in a rapid rise in blood glucose in both control and GLP-1 animals, indicating that by this time GLP-1 activity is essentially abolished. In contrast, the data of this figure clearly show that exendin-4 (Leu$_{14}$, Lys$_{20}$, Arg$_{40}$) activity at times of 240 or more minutes after first injection is preserved, since the exendin-4 (Leu$_{14}$, Lys$_{20}$, Arg$_{40}$) animals continue to buffer blood glucose levels even after the second glucose challenge.

Thus these data show not only that the exendin-4 (Leu$_{14}$, Lys$_{20}$, Arg$_{40}$) peptide preserves the glucose buffering activity of the wild-type exendin-4 peptide, but that this activity persists well past the point where other peptides, e.g., the GLP-1 peptide, are no longer active.

Example 6

The Exendin-4 Derivative Exendin-4 (Lys$_{20}$, Arg$_{40}$) Retains the Activity of Exendin-4 Activity of Buffering Blood Glucose in NOD Mice After Glucose Challenge Experiments to determine the effects on blood glucose levels of the exendin-4 derivative exendin-4 (Lys$_{20}$, Arg$_{40}$) were conducted in NOD mice provided by the Shanghai Laboratory Animal Center of Chinese Academy of Sciences. 0.9% sodium chloride solution and exendin-4 (Lys$_{20}$, Arg$_{40}$) were used in the assay. Plasma glucose testing kits were purchased from Shanghai Institute of Biological Products Ministry of Health.

Overnight-fasted NOD mice were divided into two groups. Mice in the first group were abdominally injected with 200 µl of a solution containing 40% glucose and 1 µg of exendin-4 (Lys$_{20}$, Arg$_{40}$). Mice in the second (control) group were abdominally injected were abdominally injected with a glucose solution.

30 µl of blood sample was taken from retro-orbital zeinous sinus immediately using a scaled capillary which was treated beforehand with heparin, placed into 300 µl of normal saline and mixed with the saline. Erythrocytes were removed by centrifugation at 3,000 rpm, while blood serum was kept for glucose determination. Different blood samples were taken as described above at 30 min, 60 min and 120 min, and blood serum was separated. Glucose concentrations of three plasma samples were determined according to the method described in the testing kits, and the decreasing effect of exendin-4 (Lys$_{20}$, Arg$_{40}$) on blood glucose concentration was determined.

The resulting data (not shown) demonstrate that, after dramatically increasing, the blood glucose concentration in the control group gradually returned to a normal level, while glucose concentrations in the exendin-4 (Lys$_{20}$, Arg$_{40}$) experimental group never showed a notable increase in blood glucose, and instead remained at approximately normal levels throughout the experiment. These data support the conclusion that that the administration of this exendin-4 derivatives prevents dramatic fluctuations in glucose concentration up to at least 2 hours after administration. Thus, as for the wild-type exendin-4 and exendin-4 (Leu$_{14}$, Lys$_{20}$, Arg$_{40}$) derivative discussed above, the exendin-4 (Lys$_{20}$, Arg$_{40}$) derivative is also to regulate blood glucose levels. These results also show that this activity is preserved in this exendin-4 derivative despite the amino acid changes in this peptide relative to the wild-type exendin-4 sequence.

Example 7

The Exendin-4 Derivative Exendin-4 (Lys$_{20}$, Arg$_{40}$) Exhibits an Insulinotropic Effect In order to determine whether the ability of the exendin-4 derivative exendin-4 (Lys$_{20}$, Arg$_{40}$) to decrease blood glucose in NOD mice is an insulinotropic effect, experiments were conducted to measure the effect of administration of this compound on insulin levels. In these experiments, NOD mice were provided by Shanghai Laboratory Animal Center of Chinese Academy of Sciences. 40% glucose solution, 0.9% sodium chloride solution, and exendin-4 (Lys$_{20}$, Arg$_{40}$) were used in the experiment. Insulin radioimmunoassay kits were purchased from Shanghai Institute of Biological Products Ministry of Health.

NOD mice were divided into two groups. 50 µl of blood sample was taken from the plexus venosus of the eye using a scaled capillary, the inner wall of which was rinsed with 1 mg/mL heparin and was air-dried beforehand. Mice in the two groups were abdominally injected with either 200 µl normal saline alone, or with a similar amount of saline containing 5 µg exendin-4 (Lys$_{20}$, Arg$_{40}$), respectively at t=0. Different blood samples were taken as described above at 5 min, 10 min, 20 min and 30 min. After sampling, each blood sample was immediately put into a centrifuge tube containing 50 µl of normal saline and was mixed with the saline. Erythrocytes were then removed by centrifugation at 3,000 rpm. Insulin concentrations of different samples were determined by following the methods described in the radioimmunoassay kit, and the stimulating effect of exendin-4 (Lys$_{20}$, Arg$_{40}$) on insulin secretion was determined.

The resulting data (not shown) demonstrate that abdominal injection with exendin-4 (Lys$_{20}$, Arg$_{40}$) significantly stimulates insulin secretion. Consequently, these data support the conclusion that the ability of the exendin-4 derivative exendin-4 (Lys$_{20}$, Arg$_{40}$) to decrease blood glucose in NOD mice is likely mediated by an increase in insulin levels, i.e., is an insulinotropic effect.

Example 8

Stimulating Effect f Exendin-4 (Lys$_{20}$, Arg$_{40}$) on C-peptide Secretion

In order to further investigate the insulinotropic properties of the exendin-4 derivative exendin-4 (Lys$_{20}$, Arg$_{40}$), experiments were conducted to measure the effect of administration of this compound on the production of C-peptide, which, as discussed previously, is produced in equal amounts as insulin by the cleavage of proinsulin. Healthy C57 BL mice were provided by Shanghai Laboratory Animal Center of Chinese Academy of Sciences. 40% glucose solution, 0.9% sodium chloride solution and exendin-4 (Lys$_{20}$, Arg$_{40}$) were used in the experiments. Insulin radioimmunoassay kits and C-peptide radioimmunoassay kits were purchased from Shanghai Institute of Biological Products Ministry of Health.

Healthy C57 BL mice were divided into two groups. 50 µl of blood sample was taken from plexus venosus of the eye using a scaled capillary, the inner wall of which was rinsed with 1 mg/mL heparin and was air-dried beforehand. Mice in two groups were abdominally injected with 200 µl normal saline alone, or with a similar amount of saline containing 5 µg of exendin-4 (Lys$_{20}$, Arg$_{40}$), respectively at t=0. Different blood samples were taken and, after sampling, each sample was immediately put into a centrifuge tube containing 50 µl of normal saline and was mixed with the saline. Erythrocytes were then removed by centrifugation at 3,000 rpm. The C-peptide concentration in each sample was determined by following the method described by the radioimmunoassay kit, and the stimulating effect of exendin-4 (Lys$_{20}$, Arg$_{40}$) on C-peptide secretion was determined.

The resulting data (not shown) show that the abdominal injection of exendin-4 (Lys$_{20}$, Arg$_{40}$) significantly stimulates the secretion of C-peptide relative to the control. These data therefore support the conclusion described above that the ability of the exendin-4 derivative exendin-4 (Lys$_{20}$, Arg$_{40}$) to decrease blood glucose in NOD mice is likely an insulinotropic effect.

Example 9

Construction of a Genetically Engineered Bacterial Strain Containing Multiple Copies of the Exendin-4 Derivatives Exendin-4 (Lys$_{20}$, Arg$_{40}$) by Bio-engineering Techniques The exendin-4 variant DNA encoding the exendin-4 peptide derivative exendin-4 (Lys$_{20}$, Arg$_{40}$) was synthesized based on the desired peptide sequence, as shown in FIG. 5. In order to form the exendin-4 (Lys$_{20}$, Arg$_{40}$)-encoding nucleotide sequence of FIG. 5 (SEQ ID NO:14), 6 nucleotide sequences were synthesized corresponding to the 5'-portion (SEQ ID NO: 16 and its inverse complement, SEQ ID NO: 17), middle portion (SEQ ID NO:18 and its inverse complement, SEQ ID NO:19), and 3'-portion (SEQ ID NO:20 and its inverse complement, SEQ ID NO:21) of the exendin-4 (Lys$_{20}$, Arg$_{40}$) nucleotide sequence, each sequence and its inverse complement were annealed, and the three resulting double-stranded fragments were ligated under standard conditions.

Figure 6:
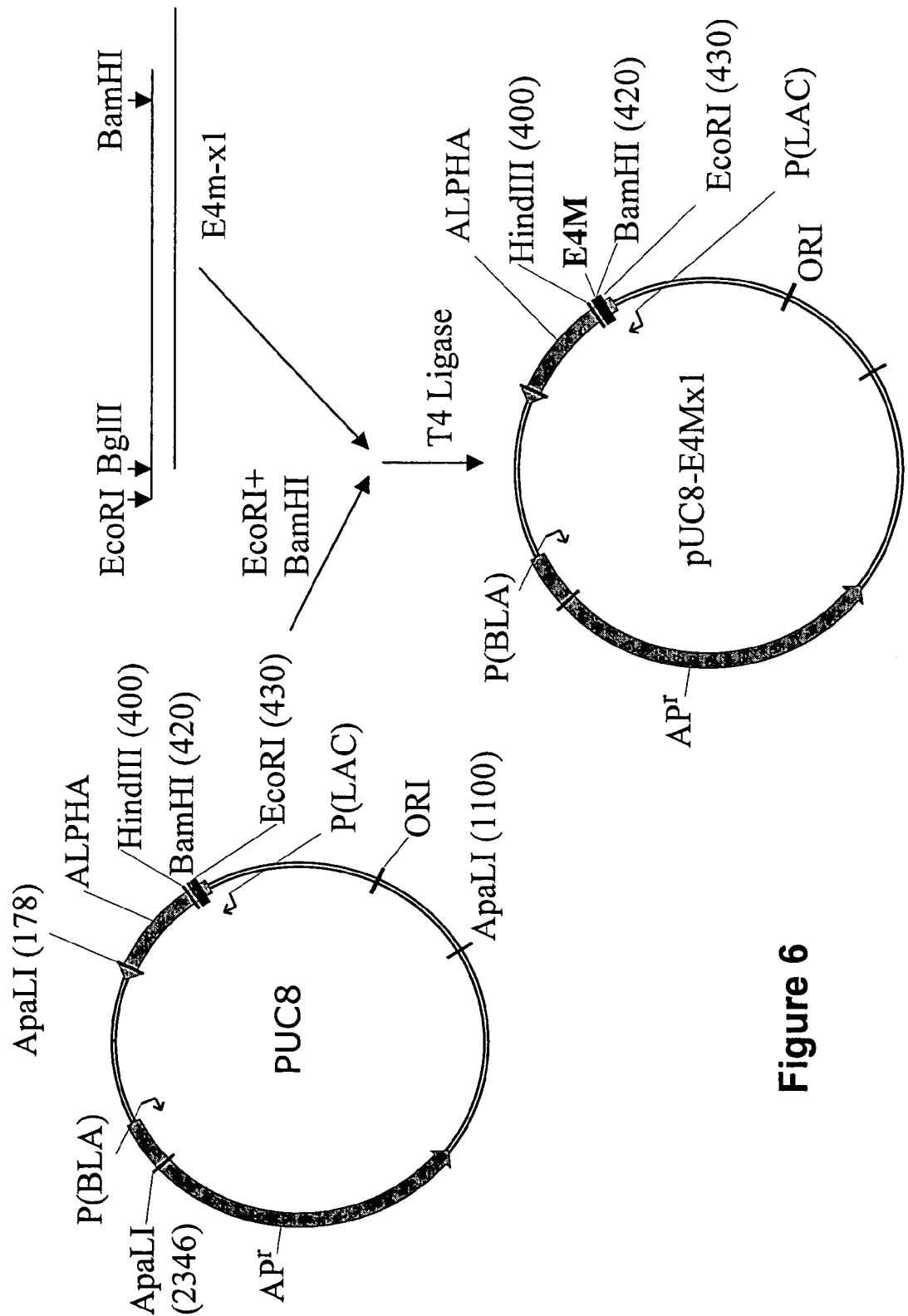
FIG. 6 shows the protocol described in Example 9 for the construction of the pUC8-EM4×1 vector containing one copy of the exendin-4 (Lys$_{20}$, Arg$_{40}$) of FIG. 5.

The resulting DNA (E4m-x1) was double digested with EcoRI and BamHI in NEB EcoRI buffer. Similar double digestion with these enzymes was also performed on pUC8, and the digested fragment of each of these two digestions were purified and ligated together with T4 ligase in the appropriate buffer under specified conditions to yield pUC8 with one copy of the exendin-4 derivative gene to form the plasmid pUC8-EM4×1. See FIG. 6 for details.

Figure 7:
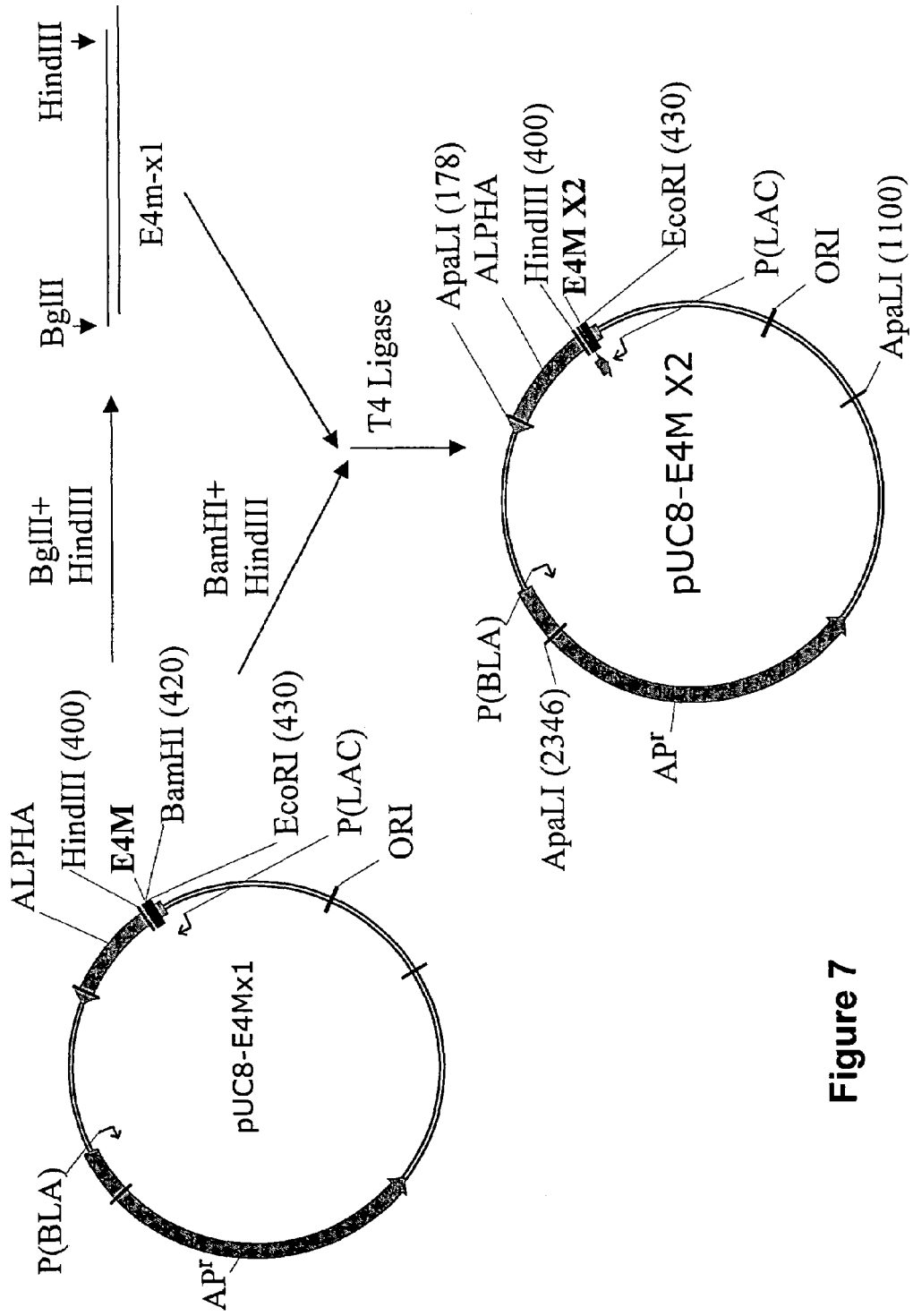
FIG. 7 shows the protocol described in Example 9 for the construction of the pUC8-EM4×2 vector containing two tandemly linked copies of the exendin-4 (Lys$_{20}$, Arg$_{40}$) of FIG. 5.

The pUC8-EM4×1 plasmid was then double digested with BamHI and HindIII to obtain the vector plus insert and, separately, the construct was double digested with BglII and Hind III to obtain the E4m-x1 insert alone. The BamHI/HindIII double digestion resulted in a linearized pUC8-Emx1 construct, which was purified and ligated to the excised E4m-x1 exendin-4 derivative insert obtained by the BglII/HindIII double digest to produce the pUC8-E4M×2 construct, which contains two copies of the exendin-4 derivative sequence. See FIG. 7 for details.

Figure 8:
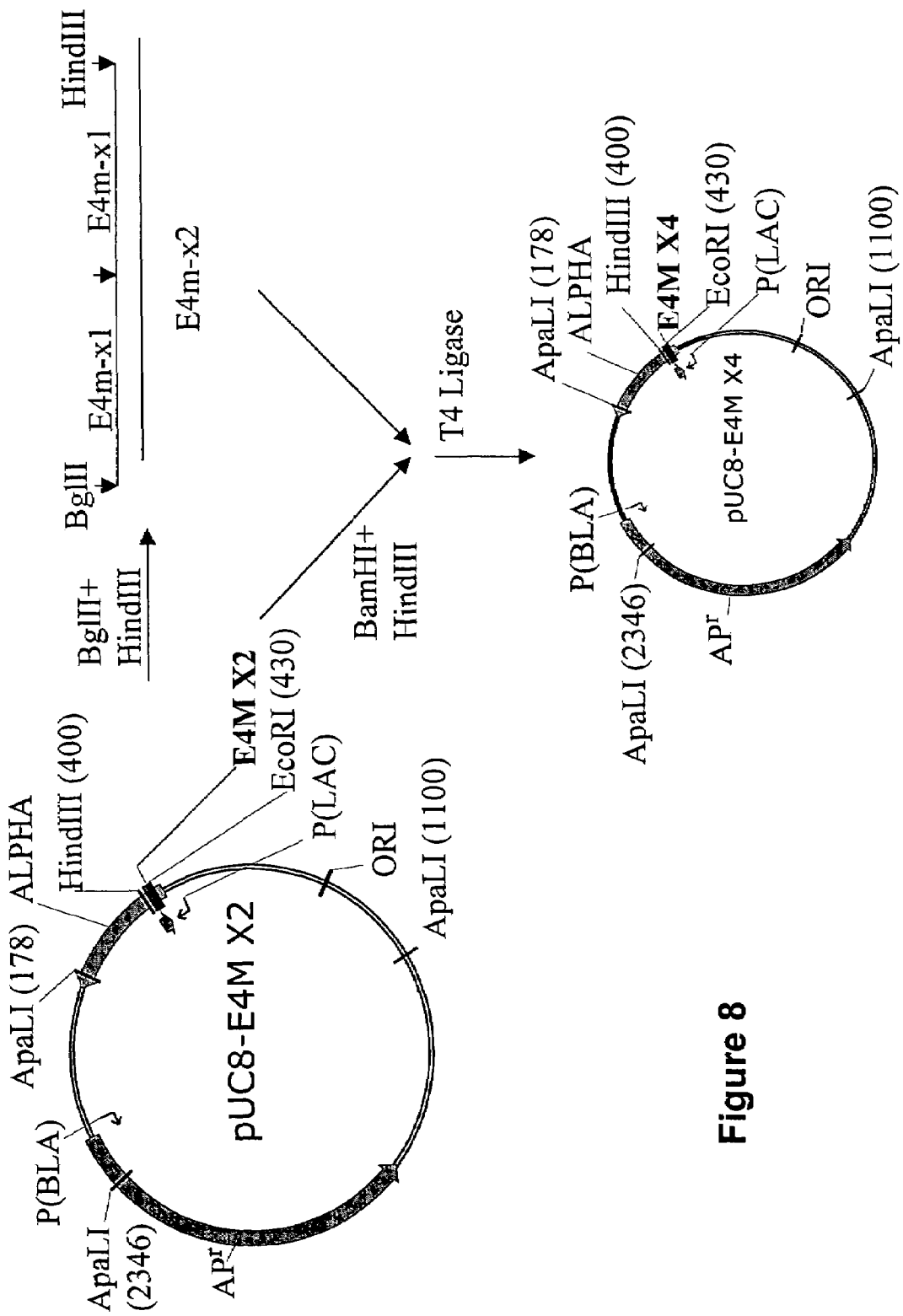
FIG. 8 shows the protocol described in Example 9 for the construction of the pUC8-EM4×4 vector containing four tandemly linked copies of the exendin-4 (Lys$_{20}$, Arg$_{40}$) of FIG. 5.
Figure 9:
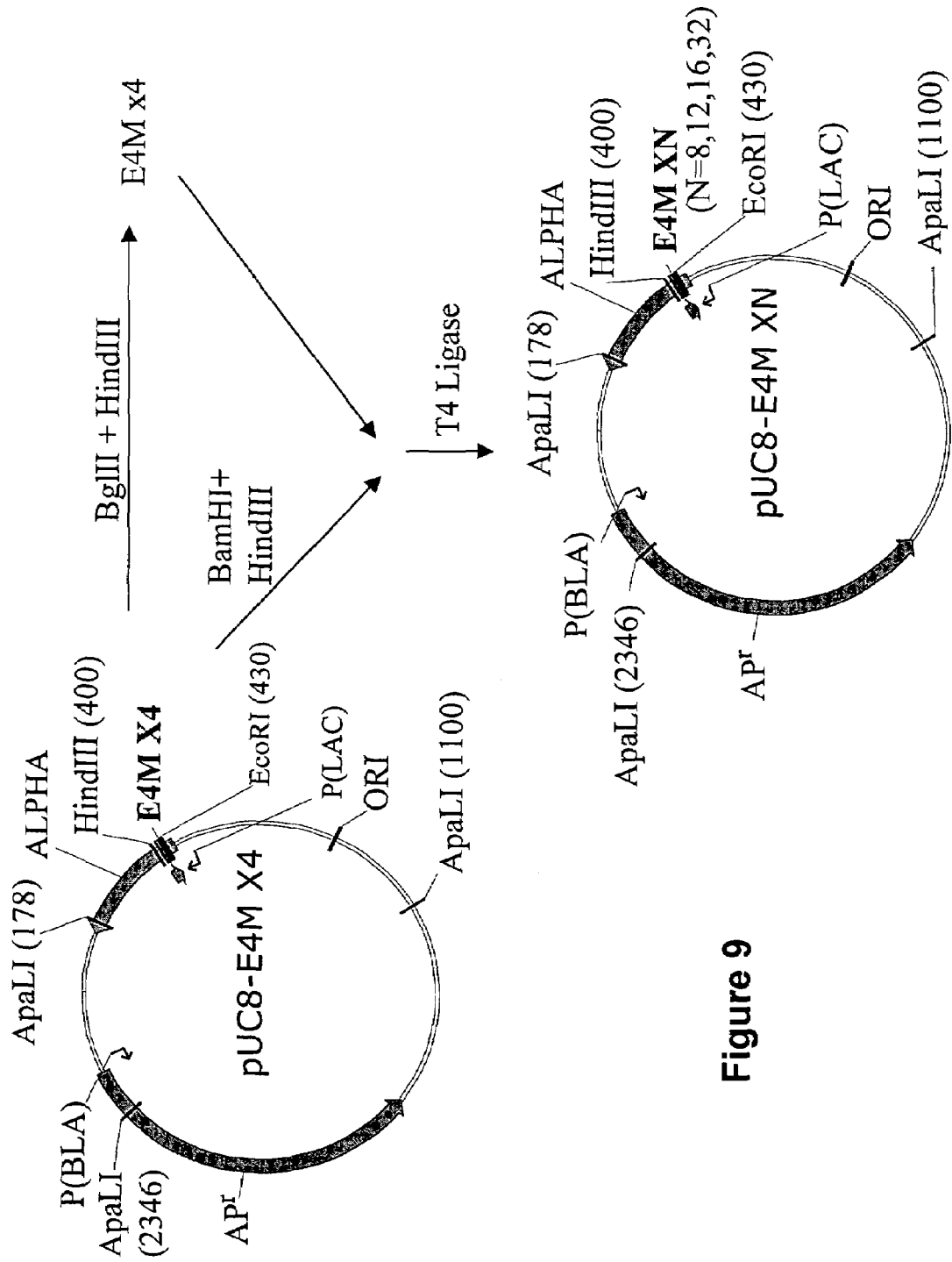
FIG. 9 shows the protocol described in Example 9 for the construction of the pUC8-EM4×N vector containing N tandemly linked copies of the exendin-4 (Lys$_{20}$, Arg$_{40}$) of FIG. 5.

Higher multimers of the desired exendin-4 peptide derivative sequence were generated using multiple repetitions of the above methods. Thus an example of the construction of a tetrameric tandemly linked exendin-4 derivative peptide is given in FIG. 8, while a generalized procedure for producing a N-mer of the exendin-4 peptide derivative sequence is given in FIG. 9.

Example 10

Fermentation of a Genetically Engineered Bacterial Strain containing an Exendin-4 Derivative Gene The fermentation of genetically engineered bacterial strains containing the exendin-4 analog gene was conducted according to the method described by Aizhen Wu et. al. ("A study of fermentation process of a genetically engineered *E. Coli,*" Chinese Journal of Biotechnology, Vol.12 supplement, pp 53-57, 1996).

A. Bacterial Seed Culture.

The culture medium for the bacterial seed culture contained 10 g/L peptone, 5 g/L yeast extracts (Difen, Sigma, or Oxoid), 20 ml of 0.2 M phosphate buffer at pH7.0, and $CaCl_2$, $Ni(NO_4)_3$, $CoCl_3$, $MgSO_4$, and $FeCl_3$ each at 1 mg/L. The medium was autoclaved for 20 minutes at 120° C. and, after cooling to 37° C., ampicillin at 50 mg/L, 20 ml of defoamer, 20 ml of seeding bacteria, and 5 ml of 20% glucose were added. The pH value was adjusted to 6.8-7.2 with 2 M NaOH and 2 M HCl, and fermentation was carried out.

B. Fermentation.

Fermentation was conducted in a 5 L, 15 L, or 150 L bioreactor (B. Braun Biostat). The conditions for fermentation were: temperature of 37° C., $P_L$ 30→42° C., agitation speed of 500 rpm, pH of 6.8-7.2, ventilation of 5 L/min, 15 L/min, or 150 L/min respectively, and $D_{O2}$ 50%.

C. Measurement of Bacterial Concentration During Fermentation.

The bacterial concentration was measured every hour by determining the wet bacterial pellet mass obtained from 1 ml aliquots of fermentation culture by centrifugation at 8,000 rpm for 10 minutes. Alternatively, the concentration can be measured by determining the density at $OD_{600\ nm}$.

Example 11

Extraction of the Inclusion Body

After fermentation, the culture medium was centrifuged at 4,000 rpm. The bacterial mass was harvested and homogenized twice for disruption at a pressure of 50 MPa in a homogenizer. The cell debris suspension was centrifuged at 6,000 rpm and the resulted supernatant was removed. After a second round of centrifugation at 10,000 rpm, the inclusion body was collected and then washed twice with 20 mM of phosphate buffer (pH 7.0) containing 10 mM of EDTA and 1% NaCl. After the inclusion body was dissolved in 8 M urea solution, the undissolved impurities were removed by centrifugation. Ultrafiltration was used to remove urea in the supernatant, and the inclusion body was harvested by centrifugation.

Example 12

Cleavage of the Inclusion Body

A. One Step Proteolysis.

The inclusion bodies resulting from fermentation of the genetically engineered bacterial strains can be cleaved by the following procedures.

A1. Use of the Protease Clostripain.

Clostripain can be used to specifically cleave the peptide bond formed by the participation of the carboxyl of an Arg residue. In this procedure, the inclusion body obtained as described above was suspended in 20 mM phosphate buffer (pH7.5), clostripain was added at a ratio of 1000:1 (protein dry weight: the amount of clostripain), and the mixture was incubated at 37° C. and continuously sampled and monitored by HPLC until all the inclusion bodies were completely cleaved. Large molecule impurities were removed with ultrafiltration (MWCO of 10,000). The exendin-4 peptide derivative was purified with preparation-scale HPLC and lyophilized to yield the desired peptide with over 99% purity.

A2. Use of the Protease Trypsin.

The protease trypsin can cleave the peptide bond formed by the participation of the carboxyl group of Lys or Arg residues. When a Lys residue is protected by anhydride, the peptide bond formed by the participation of carboxyl of Arg can be specifically cleaved by trypsin.

In this procedure, the inclusion bodies obtained as described above were dissolved into 20 mM $NaHCO_3$ solution with 1 g of the maleic anhydride derivative of conduct the acylation reaction at pH of 8.0 for 2 hours. Small molecules were removed with ultrafiltration (10,000 MWCO). The trypsin was then added at a ratio of 1000:1 (protein dry weight:the amount of trypsin). The proteolytic reaction was conducted at 37° C. and monitored with HPLC until completion of the cleavage of the inclusion bodies. The exendin-4 peptide derivative so obtained was further purified with preparation-scale HPLC and lyophilized to yield the desired peptide with over 99% purity.

Although the preferred embodiments and figures of this invention have been described in previous paragraphs, it should be apparent to one skilled in the art that modifications and alternative embodiments of this invention are possible, and substantially identical methods and substances are still within the scope of this invention, which is set forth in the following claims.

What is claimed is:

1. A peptide comprising an exendin-4 derivative peptide selected from the group consisting of SEQ ID NOs: 3, 6-8.

2. A method for the treatment of a condition involving the dysregulation of insulin levels in a patient in need thereof, said method comprises administering to said patient a therapeutically effective amount of a peptide of claim 1.

3. A method for the treatment of type II diabetes in a patient in need thereof, said method comprises administering to said patient a therapeutically effective amount of a peptide of claim 1.

4. The peptide of claim 1 wherein the amino acid residue at position 14 (Xaa 14) of SEQ ID NO:3 is Ile or Leu, and the amino acid residue at position 20 (Xaa 20) of SEQ ID NO:3 is Lys.

5. The peptide of claim 4 wherein Xaa 14 is Ile, and Xaa 20 is Lys.

6. The peptide of claim 1 wherein the amino acid residue at position 14 (Xaa 14) of SEQ ID NO:3 is Ile or Leu, and the amino acid residue at position 20 (Xaa 20) of SEQ ID NO:3 is His.

7. The peptide of claim 6 wherein Xaa 14 is Leu, and Xaa 20 is His.

* * * * *

SEQUENCE LISTING

```
<160> NUMBER OF SEQ ID NOS: 21

<210> SEQ ID NO 1
<211> LENGTH: 39
<212> TYPE: PRT
<213> ORGANISM: Heloderma horridum
<220> FEATURE:
<221> NAME/KEY: MOD_RES
<222> LOCATION: (39)..(39)
<223> OTHER INFORMATION: AMIDATION, Position 39 is Ser-NH2

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
```

-continued

```
<210> SEQ ID NO 2
<211> LENGTH: 40
<212> TYPE: PRT
<213> ORGANISM: Artificial
<220> FEATURE:
<223> OTHER INFORMATION: This sequence contains one or more substituted
                        amino acids relative to the wild-type sequence.
<220> FEATURE:
<221> NAME/KEY: MISC_FEATURE
<223> OTHER INFORMATION: The combination Xaa 14 = Met, Xaa 20 = Arg,
                        Xaa 40 = -NH2 is not allowed
<220> FEATURE:
<221> NAME/KEY: MISC_FEATURE
<222> LOCATION: (14)..(14)
<223> OTHER INFORMATION: Xaa 14 can be Arg, Ile, Leu, or Met
<220> FEATURE:
<221> NAME/KEY: MISC_FEATURE
<222> LOCATION: (20)..(20)
<223> OTHER INFORMATION: Xaa 20 can be Arg, His, or Lys
<220> FEATURE:
<221> NAME/KEY: MISC_FEATURE
<222> LOCATION: (40)..(40)
<223> OTHER INFORMATION: Xaa 40 can be -OH, -NH2, Arg-OH, or Lys-OH

<400> SEQUENCE: 2

His Gly Glu Gly Thr Phe Thr Ser Asp Leu Ser Lys Gln Xaa Glu Glu
1               5                   10                  15

Glu Ala Val Xaa Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 3
<211> LENGTH: 40
<212> TYPE: PRT
<213> ORGANISM: Artificial
<220> FEATURE:
<223> OTHER INFORMATION: This sequence contains one or more substituted
                        amino acids relative to the wild-type sequence
<220> FEATURE:
<221> NAME/KEY: misc_feature
<222> LOCATION: (14)..(14)
<223> OTHER INFORMATION: Xaa 14 can be Ile, Leu, or Met
<220> FEATURE:
<221> NAME/KEY: misc_feature
<222> LOCATION: (20)..(20)
<223> OTHER INFORMATION: Xaa 20 can be His or Lys

<400> SEQUENCE: 3

His Gly Glu Gly Thr Phe Thr Ser Asp Leu Ser Lys Gln Xaa Glu Glu
1               5                   10                  15

Glu Ala Val Xaa Leu Phe Ile Glu Trp Leu Lys Asn Gly Gly Pro Ser
            20                  25                  30

Ser Gly Ala Pro Pro Pro Ser Arg
        35                  40

<210> SEQ ID NO 4
<211> LENGTH: 40
<212> TYPE: PRT
<213> ORGANISM: Artificial
<220> FEATURE:
<223> OTHER INFORMATION: This sequence contains one or more substituted
                        amino acids relative to the wild-type sequence
<220> FEATURE:
<221> NAME/KEY: misc_feature
<222> LOCATION: (12)..(12)
<223> OTHER INFORMATION: Xaa 12 is not Arg or Lys
<220> FEATURE:
```

```
<221> NAME/KEY: misc_feature
<222> LOCATION: (20)..(20)
<223> OTHER INFORMATION: Xaa 20 is not Arg or Lys
<220> FEATURE:
<221> NAME/KEY: misc_feature
<222> LOCATION: (27)..(27)
<223> OTHER INFORMATION: Xaa 27 is not Arg or Lys

<400> SEQUENCE: 4

His Gly Glu Gly Thr Phe Thr Ser Asp Leu Ser Xaa Gln Met Glu Glu
1               5                   10                  15

Glu Ala Val Xaa Leu Phe Ile Glu Trp Leu Xaa Asn Gly Gly Pro Ser
            20                  25                  30

Ser Gly Ala Pro Pro Pro Ser Arg
        35                  40

<210> SEQ ID NO 5
<211> LENGTH: 40
<212> TYPE: PRT
<213> ORGANISM: Artificial
<220> FEATURE:
<223> OTHER INFORMATION: This sequence contains one or more substituted
                        amino acids relative to the wild-type sequence
<220> FEATURE:
<221> NAME/KEY: misc_feature
<222> LOCATION: (20)..(20)
<223> OTHER INFORMATION: Xaa 20 is not Arg or Lys

<400> SEQUENCE: 5

His Gly Glu Gly Thr Phe Thr Ser Asp Leu Ser Lys Gln Met Glu Glu
1               5                   10                  15

Glu Ala Val Xaa Leu Phe Ile Glu Trp Leu Lys Asn Gly Gly Pro Ser
            20                  25                  30

Ser Gly Ala Pro Pro Pro Ser Arg
        35                  40

<210> SEQ ID NO 6
<211> LENGTH: 40
<212> TYPE: PRT
<213> ORGANISM: Artificial
<220> FEATURE:
<223> OTHER INFORMATION: This sequence contains one or more substituted
                        amino acids relative to the wild-type sequence.

<400> SEQUENCE: 6

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser Arg
        35                  40

<210> SEQ ID NO 7
<211> LENGTH: 40
<212> TYPE: PRT
<213> ORGANISM: Artificial
<220> FEATURE:
<223> OTHER INFORMATION: This sequence contains one or more substituted
                        amino acids relative to the wild-type sequence

<400> SEQUENCE: 7

His Gly Glu Gly Thr Phe Thr Ser Asp Leu Ser Lys Gln Met Glu Glu
1               5                   10                  15

Glu Ala Val His Leu Phe Ile Glu Trp Leu Lys Asn Gly Gly Pro Ser
            20                  25                  30
```

Ser Gly Ala Pro Pro Pro Ser Arg
    35                  40

<210> SEQ ID NO 8
<211> LENGTH: 40
<212> TYPE: PRT
<213> ORGANISM: Artificial
<220> FEATURE:
<223> OTHER INFORMATION: This sequence contains one or more substituted
                        amino acids relative to the wild-type sequence.

<400> SEQUENCE: 8

His Gly Glu Gly Thr Phe Thr Ser Asp Leu Ser Lys Gln Leu Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser Arg
    35                  40

<210> SEQ ID NO 9
<211> LENGTH: 30
<212> TYPE: PRT
<213> ORGANISM: Homo sapiens

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 10
<211> LENGTH: 68
<212> TYPE: DNA
<213> ORGANISM: Artificial
<220> FEATURE:
<223> OTHER INFORMATION: Exendin-4 synthetic sequence

<400> SEQUENCE: 10
aattccatgc acggcgaagg caccttcacc agcgatctga gcaaacagct ggaagaagaa    60
gcggttaa                                                             68

<210> SEQ ID NO 11
<211> LENGTH: 65
<212> TYPE: DNA
<213> ORGANISM: Artificial
<220> FEATURE:
<223> OTHER INFORMATION: Exendin-4 synthetic sequence

<400> SEQUENCE: 11
actgttcatc gaatggctga aaaacggcgg cccgagcagc ggcgcgccgc cgccgagccg    60
ttaga                                                                65

<210> SEQ ID NO 12
<211> LENGTH: 64
<212> TYPE: DNA
<213> ORGANISM: Artificial
<220> FEATURE:
<223> OTHER INFORMATION: Exendin-4 synthetic sequence

<400> SEQUENCE: 12
agcttctaac ggctcggcgg cggcgcgccg ctgctcgggc cgccgttttt cagccattcg    60
atga                                                                 64

<210> SEQ ID NO 13
<211> LENGTH: 69
<212> TYPE: DNA
<213> ORGANISM: Artificial
<220> FEATURE:
<223> OTHER INFORMATION: Exendin-4 synthetic sequence

<400> SEQUENCE: 13
acagtttaac cgcttcttct tccagctgtt tgctcagatc gctggtgaag gtgccttcgc    60
cgtgcatgg                                                           69

<210> SEQ ID NO 14
<211> LENGTH: 147
<212> TYPE: DNA
<213> ORGANISM: Artificial
<220> FEATURE:
<223> OTHER INFORMATION: Exendin-4 synthetic sequence

<400> SEQUENCE: 14
aattccagat ctatgcgtca cggcgaaggc accttcacca gcgatctgag caaacagatg    60
gaagaagaag cggttaaact gttcatcgaa tggctgaaaa acggcggccc gagcagcggc   120
gcgccgccgc cgagccgtgg atcctag                                       147

<210> SEQ ID NO 15
<211> LENGTH: 133
<212> TYPE: DNA
<213> ORGANISM: Artificial
<220> FEATURE:
<223> OTHER INFORMATION: Exendin-4 synthetic sequence

<400> SEQUENCE: 15
aattccatgc acggcgaagg caccttcacc agcgatctga gcaaacagct ggaagaagaa    60
gcggttaaac tgttcatcga atggctgaaa aacggcggcc cgagcagcgg cgcgccgccg   120
ccgagccgtt aga                                                      133

<210> SEQ ID NO 16
<211> LENGTH: 39
<212> TYPE: DNA
<213> ORGANISM: Artificial
<220> FEATURE:
<223> OTHER INFORMATION: Exendin-4 synthetic sequence

<400> SEQUENCE: 16
aattccagat ctatgcgtca cggcgaaggc accttcacc                          39

<210> SEQ ID NO 17
<211> LENGTH: 41
<212> TYPE: DNA
<213> ORGANISM: Artificial
<220> FEATURE:
<223> OTHER INFORMATION: Exendin-4 synthetic sequence

<400> SEQUENCE: 17
atcgctggtg aaggtgcctt cgccgtgacg catagatctg g                       41

<210> SEQ ID NO 18
<211> LENGTH: 51
<212> TYPE: DNA
<213> ORGANISM: Artificial
<220> FEATURE:
<223> OTHER INFORMATION: Exendin-4 synthetic sequence

```
<400> SEQUENCE: 18
agcgatctga gcaaacagat ggaagaagaa gcggttaaac tgttcatcga a          51

<210> SEQ ID NO 19
<211> LENGTH: 51
<212> TYPE: DNA
<213> ORGANISM: Artificial
<220> FEATURE:
<223> OTHER INFORMATION: Exendin-4 synthetic sequence

<400> SEQUENCE: 19
cagccattcg atgaacagtt taaccgcttc ttcttccatc tgtttgctca g          51

<210> SEQ ID NO 20
<211> LENGTH: 57
<212> TYPE: DNA
<213> ORGANISM: Artificial
<220> FEATURE:
<223> OTHER INFORMATION: Exendin-4 synthetic sequence

<400> SEQUENCE: 20
tggctgaaaa acggcggccc gagcagcggc gcgccgccgc cgagccgtgg atcctag    57

<210> SEQ ID NO 21
<211> LENGTH: 55
<212> TYPE: DNA
<213> ORGANISM: Artificial
<220> FEATURE:
<223> OTHER INFORMATION: Exendin-4 synthetic sequence

<400> SEQUENCE: 21
gatcctagga tccacggctc ggcggcggcg cgccgctgct cgggccgccg ttttt      55
```